(12) United States Patent
Brown et al.

(10) Patent No.: US 7,831,444 B2
(45) Date of Patent: *Nov. 9, 2010

(54) REMOTE HEALTH MANAGEMENT SYSTEM

(75) Inventors: Stephen J. Brown, Woodside, CA (US); Gowthaman Gunabushanam, Hyderabad (IN)

(73) Assignee: Health Hero Network, Inc., Palo Alto, CA (US)

( * ) Notice: Subject to any disclaimer, the term of this patent is extended or adjusted under 35 U.S.C. 154(b) by 371 days.

This patent is subject to a terminal disclaimer.

(21) Appl. No.: 11/689,721

(22) Filed: Mar. 22, 2007

(65) Prior Publication Data

US 2007/0179361 A1 Aug. 2, 2007

Related U.S. Application Data

(63) Continuation of application No. 10/356,720, filed on Jan. 30, 2003, now abandoned, and a continuation-in-part of application No. 11/272,816, filed on Nov. 15, 2005, now Pat. No. 7,613,590, which is a continuation-in-part of application No. 09/422,046, filed on Oct. 20, 1999, now Pat. No. 7,624,028, which is a continuation of application No. 09/271,217, filed on Mar. 17, 1999, now Pat. No. 6,168,563, which is a continuation-in-part of application No. 08/946,341, filed on Oct. 7, 1997, now Pat. No. 5,997,476, which is a continuation-in-part of application No. 08/847,009, filed on Apr. 30, 1997, now Pat. No. 5,897,493, and a continuation-in-part of application No. 08/481,925, filed on Jun. 7, 1995, now Pat. No. 5,899,855, which is a continuation of application No. 08/233,397, filed on Apr. 26, 1994, now abandoned, which is a continuation of application No. 07/977,323, filed on Nov. 17, 1992, now Pat. No. 5,307,263.

(60) Provisional application No. 60/379,330, filed on May 8, 2002, provisional application No. 60/041,746, filed on Mar. 28, 1997, provisional application No. 60/041,751, filed on Mar. 28, 1997.

(51) Int. Cl.
*G06Q 10/00* (2006.01)

(52) U.S. Cl. .......................................................... 705/2

(58) Field of Classification Search .................. 705/2–3
See application file for complete search history.

(56) References Cited

U.S. PATENT DOCUMENTS 4,130,881 A 12/1978 Haessler et al.

(Continued)

FOREIGN PATENT DOCUMENTS

EP 0320749 6/1989

(Continued)

OTHER PUBLICATIONS

+5V Powered Isolated RS-232 Drivers/Receivers Maxim Integrated Products.

(Continued)

*Primary Examiner*—Robert W Morgan
(74) *Attorney, Agent, or Firm*—Christopher P. Maiorana, PC

(57) ABSTRACT

A system and method that remotely accesses and diagnoses the medical condition of an individual patient and of each patient in a group of patients and provides treatment based upon the diagnoses of the individual patient and the risk stratification the individual patient assumes in the group of patients.

12 Claims, 12 Drawing Sheets

U.S. PATENT DOCUMENTS

| | | |
|---|---|---|
| 4,151,407 A | 4/1979 | McBride et al. |
| 4,253,521 A | 3/1981 | Savage |
| 4,347,568 A | 8/1982 | Giguere et al. |
| 4,347,851 A | 9/1982 | Jundanian |
| 4,360,345 A | 11/1982 | Hon |
| 4,546,436 A | 10/1985 | Schneider et al. |
| 4,576,578 A | 3/1986 | Parker et al. |
| 4,729,381 A | 3/1988 | Harada et al. |
| 4,731,726 A | 3/1988 | Allen, III |
| 4,768,229 A | 8/1988 | Benjamin et al. |
| 4,779,199 A | 10/1988 | Yoneda et al. |
| 4,796,639 A | 1/1989 | Snow et al. |
| 4,799,199 A | 1/1989 | Scales, III et al. |
| 4,803,625 A | 2/1989 | Fu et al. |
| 4,858,354 A | 8/1989 | Gettler |
| 4,897,869 A | 1/1990 | Takahashi |
| 4,907,973 A | 3/1990 | Hon |
| 4,933,873 A | 6/1990 | Kaufman et al. |
| 4,950,246 A | 8/1990 | Muller |
| 5,007,429 A | 4/1991 | Treatch et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,056,059 A | 10/1991 | Tivig et al. |
| 5,065,315 A | 11/1991 | Garcia |
| 5,068,536 A | 11/1991 | Rosenthal |
| 5,077,476 A | 12/1991 | Rosenthal |
| 5,095,798 A | 3/1992 | Okada et al. |
| 5,109,974 A | 5/1992 | Beer et al. |
| 5,111,817 A | 5/1992 | Clark et al. |
| 5,120,230 A | 6/1992 | Clark et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,176,502 A | 1/1993 | Sanderson et al. |
| 5,182,707 A | 1/1993 | Cooper et al. |
| 5,204,670 A | 4/1993 | Stinton |
| 5,222,020 A | 6/1993 | Takeda |
| 5,227,874 A | 7/1993 | Von Kohorn |
| 5,249,044 A | 9/1993 | Von Kohorn |
| 5,262,943 A | 11/1993 | Thibado et al. |
| 5,299,121 A | 3/1994 | Brill et al. |
| 5,307,263 A | 4/1994 | Brown |
| 5,329,459 A | 7/1994 | Kaufman et al. |
| 5,329,608 A | 7/1994 | Bocchieri et al. |
| 5,331,549 A | 7/1994 | Crawford, Jr. |
| 5,339,821 A | 8/1994 | Fujimoto |
| 5,341,291 A | 8/1994 | Roizen et al. |
| 5,344,324 A | 9/1994 | O'Donnell et al. |
| 5,357,427 A | 10/1994 | Langen et al. |
| 5,366,896 A | 11/1994 | Margrey et al. |
| 5,544,649 A | 8/1996 | David et al. |
| 5,549,117 A | 8/1996 | Tacklind et al. |
| 5,550,575 A | 8/1996 | West et al. |
| 5,553,609 A | 9/1996 | Chen et al. |
| 5,558,638 A | 9/1996 | Evers et al. |
| 5,569,212 A | 10/1996 | Brown |
| 5,572,421 A | 11/1996 | Altman et al. |
| 5,574,828 A | 11/1996 | Hayward et al. |
| 5,576,952 A | 11/1996 | Stutman et al. |
| 5,596,994 A | 1/1997 | Bro |
| 5,597,307 A | 1/1997 | Redford et al. |
| 5,601,435 A | 2/1997 | Quy |
| 5,619,991 A | 4/1997 | Sloane |
| 5,624,265 A | 4/1997 | Redford et al. |
| 5,628,309 A | 5/1997 | Brown |
| 5,631,844 A | 5/1997 | Margrey et al. |
| 5,633,910 A | 5/1997 | Cohen |
| 5,642,731 A | 7/1997 | Kehr |
| 5,642,936 A | 7/1997 | Evans |
| 5,670,711 A | 9/1997 | Detournay et al. |
| 5,675,635 A | 10/1997 | Vos et al. |
| 5,678,562 A | 10/1997 | Sellers |
| 5,687,322 A | 11/1997 | Deaton et al. |
| 5,687,717 A | 11/1997 | Halpern et al. |
| 5,704,366 A | 1/1998 | Tacklind et al. |
| 5,704,902 A | 1/1998 | Vandenbelt et al. |
| 5,711,297 A | 1/1998 | Iliff |
| 5,715,451 A | 2/1998 | Marlin |
| 5,717,913 A | 2/1998 | Driscoll |
| 5,720,733 A | 2/1998 | Brown |
| 5,722,418 A | 3/1998 | Bro |
| 5,727,153 A | 3/1998 | Powell |
| 5,732,709 A | 3/1998 | Tacklind et al. |
| 5,752,234 A | 5/1998 | Withers |
| 5,760,771 A | 6/1998 | Blonder et al. |
| 5,772,585 A | 6/1998 | Lavin et al. |
| 5,782,814 A | 7/1998 | Brown et al. |
| 5,785,650 A | 7/1998 | Akasaka et al. |
| 5,791,342 A | 8/1998 | Woodard |
| 5,792,117 A | 8/1998 | Brown |
| 5,793,969 A | 8/1998 | Kamentsky et al. |
| 5,796,393 A | 8/1998 | MacNaughton et al. |
| 5,802,494 A | 9/1998 | Kuno |
| 5,810,747 A | 9/1998 | Brudny et al. |
| 5,819,735 A | 10/1998 | Mansfield et al. |
| 5,822,544 A | 10/1998 | Chaco et al. |
| 5,825,283 A | 10/1998 | Camhi |
| 5,827,180 A | 10/1998 | Goodman |
| 5,828,943 A | 10/1998 | Brown |
| 5,835,896 A | 11/1998 | Fisher et al. |
| 5,868,669 A | 2/1999 | Iliff |
| 5,875,432 A | 2/1999 | Sehr |
| 5,879,163 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hofbert et al. |
| 5,924,074 A * | 7/1999 | Evans ........................... 705/3 |
| 5,933,136 A | 8/1999 | Brown |
| 5,961,446 A | 10/1999 | Beller et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 6,001,065 A | 12/1999 | DeVito |
| 6,022,315 A | 2/2000 | Iliff |
| 6,022,615 A | 2/2000 | Rettenbacher |
| 6,029,138 A | 2/2000 | Khorasani et al. |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,081,786 A * | 6/2000 | Barry et al. ..................... 705/3 |
| 6,110,148 A | 8/2000 | Brown et al. |
| 6,138,145 A | 10/2000 | Kawanaka |
| 6,151,586 A | 11/2000 | Brown |
| 6,168,563 B1 * | 1/2001 | Brown ....................... 600/301 |
| 6,177,940 B1 | 1/2001 | Bond et al. |
| 6,189,029 B1 | 2/2001 | Fuerst |
| 6,248,065 B1 | 6/2001 | Brown |

| | | |
|---|---|---|
| 2002/0035486 A1* | 3/2002 | Huyn et al. .................... 705/3 |

FOREIGN PATENT DOCUMENTS

| | | |
|---|---|---|
| EP | 370599 | 5/1990 |
| EP | 0461910 | 12/1991 |
| EP | 508912 | 10/1992 |
| EP | 526166 | 2/1993 |
| EP | 676709 | 10/1995 |
| EP | 680727 | 11/1995 |
| EP | 761160 | 3/1997 |
| EP | 0251520 | 1/1998 |
| GB | 2218831 | 11/1989 |
| JP | 62226278 | 10/1987 |
| WO | WO 9302622 | 2/1993 |
| WO | WO 9416774 | 8/1994 |
| WO | WO 95/09386 | 4/1995 |
| WO | WO 95/20199 | 7/1995 |
| WO | WO 96/25877 | 8/1996 |
| WO | WO 97/08605 | 3/1997 |
| WO | WO 97/12544 | 4/1997 |
| WO | WO 98/16895 | 4/1998 |

OTHER PUBLICATIONS

Anonymous, "Health Hero Network, Inc. Receives First-Ever FDA Clearance for Connecting Medical Devices to Internet", PR Newswire, (Dec. 2, 1993), 3 pages.

Bower, "Brain Clues to Energy-efficient Learning", Science News, (Apr. 1992), v. 141; p. 215(1); Dialog: File 647, Acct# 12123949.

Bruce, "Health Hero Network CEO, CNNfn", Digital Jam, (Dec. 1, 1999), 3.

Bruce, et al., "The Effects of Sympathetic Nervous System Activation and Psychological Stress . . . "; Diabetologia; 35(9); 1992; 835-843; Dialog: File 5, Acc#9629427. (9 pages).

CD-ROM Mavericks: Proprietary TV-Based Players, Byte Guide to CD-ROM, pp. 100-105.

Finston, "Parent + Teacher = Healthy Child", Diabetes Forecast, (Apr. 1994), v47 n9; p. 26(5); Dialog: file 149, Acc# 15804228.

Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.

Guiffrida, et al., Should We Pay the Patient? Review of Financial Incentives to enhance Patient Compliance:, Biomedical Journal, (1997), vol. 315, pp. 703-707.

Hunter, "Technological Advances in Bedside Monitoring: Biosensors", Archives and Laboratory Medicine, (Jul. 1987), pp. 633-636.

Introducing the Next Generation of About Your Diabetes, U.S. Pharmacopical Convention and American Diabetes Association, (1993).

Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.

Marsh, David G. "Approaches Toward the Genetic Analysis of Complex Traits Asthma and Atrophy", Am. J. Respir.Crit.Care Med., (1997), vol. 156, pp. S-133-S138.

Martinez, Fernando D., "Complexities of the Genetics of Asthma", Am.J. Respir. Crit. Care Med., (1997), vol. 156, pp. S117-S122.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

Meissner, et al., "Building an Integrated Clinical and Research Network", Proceedings of the SPIE, (Oct. 24, 1995), vol. 2618, p. 92-99.

Moore, "New Applications Break Through Storage Boundaries", Computer Technology Review, (Oct. 1999), vol. 19, No. 10 p. 1.

Reis, H, "Telemedicine: Transmitting Expertise to the Point of Care Toward an Electronic Patient Record"; '97, Nashville, TN, Apr. 27-May 3, 1997, pp. 248-256, v. 3.

Roberts; "Diabetes and Stress: A Type A Connection?", Psychology Today, (Jul. 1987), v. 21; pp. 22(1); Dialog: File 149, Acc# 05038381.

Schork, Nicholas J., "Genetics of Complex Disease", Am.J.Respir. Crit. Care Me., (1997), vol. 156, pp. S103-S109.

Shandle, Jack, "Who Will Dominate The Desktop in the 90's?", , Electronics, Feb. 1990, pp. 48-50. (3 pages) Cited by 2 patents.

Voelker, Rebecca, "Shoe Leather Therapy is Gaining on TB", Jama, (Mar. 13, 1996), vol. 275, 743.

* cited by examiner

100R — REGISTRATION DIALOG

- 160 — CURRENT HEALTH CONDITION
  - 162 — CURRENT DISEASE SYMPTOMS
  - 164 — PATTERN, HISTORY DATA

- 166 — MOTIVATIONAL DRIVERS
  - 168 — LONGEVITY
  - 170 — QUALITY OF LIFE
  - 172 — FAMILY LIFE
  - 174 — SOCIAL RESPONSIBILITY
  - 175 — SOCIAL ACCEPTABILITY
  - 176 — ECONOMY

- 178 — COMPREHENSION CAPACITY
  - 180 — AGE
  - 182 — LANGUAGE SKILLS
  - 184 — READING HABITS
  - 186 — EDUCATIONAL BACKGROUND

- 188 — PREFERRED MEDIA
  - 190 — PICTURES
  - 192 — TEXT
  - 194 — VIDEO GAMES

FIG. 6

REMOTE HEALTH MANAGEMENT SYSTEM

This application is a continuation of U.S. application Ser. No. 10/356,720, filed Jan. 30, 2003 now abandoned, which claims priority to U.S. provisional application Ser. No. 60/379,330, filed May 8, 2002.

This application is a continuation in-part of Ser. No. 11/272,816, filed Nov. 15, 2005 now U.S. Pat. No. 7,613,590, which is a continuation in-part of application Ser. No. 09/422, 046, filed Oct. 20, 1999 now U.S. Pat. No. 7,624,028, which is a continuation of application Ser. No. 09/271,217, filed Mar. 17, 1999, now U.S. Pat. No. 6,168,563, which is (A) a continuation in-part of application Ser. No. 08/946,341, filed Oct. 7, 1997, now U.S. Pat. No. 5,997,476, which is a continuation in-part of application Ser. No. 08/847,009, filed Apr. 30, 1997, now U.S. Pat. No. 5,897,493, which claims the benefit of Provisional application 60/041,746, filed Mar. 28, 1997 and provisional application 60/041,751, filed Mar. 28, 1997 and (B) a continuation in-part of application Ser. No. 08/481,925, filed Jun. 7, 1995, now U.S. Pat. No. 5,899,855, which is a continuation of application Ser. No. 08/233,397, filed Apr. 26, 1994, now abandoned, which is a continuation of application Ser. No. 07/977,323, filed Nov. 17, 1992, now U.S. Pat. No. 5,307,263. All of the above-identified applications are incorporated herein by reference in their entirety.

The present application is related to U.S. Pat. Nos. 6,168, 563; 6,101,478; 5,897,493; 5,307,263; 5,899,855; 6,381,577; 6,248,065; and 6,368,273, which are hereby incorporated by reference in their entirety.

FIELD OF THE INVENTION

The present invention relates to a modular interactive system and method for remote health management, and in particular to an automated content delivery program able to connect remote users across independent platforms to a central database of libraries whereby a patient's health can be scored dynamically, and appropriate health management methods may be instituted that is appropriate for the patient's health profile, disease state, comprehension capacity, personal attitudes and medical needs, including that due to co-morbid conditions.

BACKGROUND OF THE INVENTION

The invention relates to the field of health management, particularly to an automated interactive system and method for remotely interacting across independent platforms with a group of patients with one or more disease states, and with additionally possible co-morbid conditions on a regular basis with a purpose to educate and inform the individual about his/her health condition, to motivate the individual to change health related behavior, secure compliance with medical regimens, to monitor health related parameters, and to intervene early with an ultimate view to improve the health status of the individual monitored client.

In the United States alone, over 100 million people have chronic health conditions, accounting for an estimated $700 billion in annual medical costs. Because of the continuous nature of these health conditions, and in an effort to control these medical costs, many healthcare providers have initiated outpatient or home healthcare programs for their patients. The success of these programs is dependent upon the healthcare provider's ability to effectively monitor patients remotely, and to detect and intervene at an early stage in order to prevent the patient's medical state from becoming more complicated, expensive and difficult to manage. In addition, the program's success is also dependent on its sustaining the patient's interest and continued participation in a process that often extends to the remaining term of an individual's life.

Managing a chronic disease or ongoing health condition often requires the monitoring and controlling of a physical or mental parameter relating to the health condition. Examples of these parameters include blood glucose in diabetes, respiratory flow in asthma, blood pressure in hypertension, cholesterol in cardiovascular disease, weight in eating disorders, T-cell or viral count in HIV, and frequency, severity or timing of episodes in mental health disorders.

Since the patients themselves monitor their health condition, the clinician is often limited to learning each patient's status strictly through patient initiated events, such as an emergency visit, an urgent care visit, a phone call, or other patient initiated event that results in delivery of the patient's latest medical data. Even with the current availability of remote monitoring devices that store and transmit medical data from a patient's home to a clinic, the clinician must still wait for medical information whose arrival depends on the patient's initiative.

As a result, the majority of the clinician's time is spent with the patients who are the most motivated and eager for a response, or patients whose conditions have become acute and require immediate attention, while the greatest opportunity to improve care and prevent conditions from exacerbating remain unknown and hidden with the less motivated or "pre-acute" patients who do not visit the clinician or transmit their medical data.

The less motivated patients often develop urgent medical needs that could have been prevented with prior medical management. Consequently, the cost of treating their chronic health conditions is much higher than one might expect given the sophistication of current medical monitoring devices.

In addition, the management of well motivated patients differs considerably from the strategy employed in managing high risk patients who aren't driven to initiate care because they do not perceive a crisis or are less motivated to change their behavior. Thus it is important to determine the level of motivation in the individual patient when deciding the plan of management.

A patient health status reporting system that summarizes and stratifies by risk-potential, the data received from the patients as a group would help the healthcare provider identify those patients who are in the greatest need of the provider's attention, and would help increase the provider's efficiency and productivity.

Unfortunately, most existing healthcare information systems are only designed to display medical data on an individual patient basis. Few systems have been developed that enable clinicians to view medical data for an entire group of patients simultaneously. Consequently, it is extremely difficult for a healthcare provider, such as a clinician or a nurse to prioritize his or her time and efforts in a manner that optimizes care and minimizes costs and complications for a given group of patients.

The success of a health management program in chronic health condition also depends on the program's ability to modify the health related behaviors of the patient. Examples include changing the dietary habits, and exercising habits in a patient with diabetes; smoking cessation in patients, who have suffered heart attacks, etc. A patient's compliance to medical advice varies considerably with the patient's perception of his/her health condition, healthcare provider; level of knowledge regarding his/her health condition, personal beliefs, motivational drivers, etc. In order that that the patient receives the best medical advice, and with a view to improve the ultimate prognosis of an individual with a given condition, it becomes necessary that the healthcare management plan takes into account the above factors, and that it is customized to the individual.

Notwithstanding the methods to improve the compliance in the patient, with patients on prolonged follow up, there often develops resistance to the health management plan. This resistance may develop as a result of symptom-relief in the patient and his/her consequent inability to appreciate that the underlying disease process is unchanged or may be worsening (the patient feels that he/she 'doesn't need the medication anymore'). It may also develop in response to the nature of content presented to the individual i.e. the patient finds queries regarding a particular context intrusive to his/her lifestyle. It is important to detect resistance early and suitably modify content so as to prevent the further development of resistance, and improve compliance in the patient.

In some diseases such as asthma and allergy, and in the mental health conditions, the precise diagnosis is not always known to the healthcare provider. Further, in these conditions, even after the diagnosis is made, the best treatment is not always clear and may need to be evaluated over time. In these patients, dynamic monitoring of the patient may help understand the condition better, and formulate the ideal medical management plan in the given patient.

It is also important to determine the reliability, consistency and accuracy levels of the information that is inputted into the system, given that the future medical management of the patient is dependent on this data. This is especially more so in those cases where the data provided by the patient is the only source of information, and in the field of medical research.

Additionally, in the field of medical research, it is necessary to analyze the patient data in order to better understand patient diagnosis and needs. The system presents a method by which routinely collected data from patients over multiple healthcare facilities may be integrated and this information may be used to understand subgroups of patients who may respond differently to treatment or benefit from different treatment options. In addition, the invention also presents a method by which patients may be selected for enrollment in studies.

Further, it is also advantageous that any remote health management system be compatible with a range of communication protocols and devices, in order that the patient communicates using the media and remote apparatuses that he/she is most comfortable in using, and has ready access to. Differing remote apparatuses and communication networks have varying requirements and limitations and advantages with regard to data display and transfer. There are advantages with specific media that may be utilized in ensuring a more satisfying interaction of the patient with the healthcare provider, a greater involvement in the disease management process, and ultimately a better prognosis in the patient's disease state. Current systems are incapable of automatically optimizing content to the remote apparatus, type and speed of communication network, and to individual preferences.

Current systems are incapable of automatically administering a management plan that is relevant to patient's profile, updating the profile in response to replies received from the interaction, and highlighting to the provider those aspects of the patient's condition that require his/her greatest attention. Current systems are also incapable of risk-stratifying the individual patients within the group.

Current systems lack the capability to analyze the reliability, consistency and veracity of the replies, and validate the information inputted into the system. Further, there is no system in place that enables a researcher or a healthcare provider to select research subjects either prospectively or retrospectively for study on the basis of data contained within the profile. Current systems do not easily allow the collected data to be integrated over multiple healthcare facilities and utilized for the purpose of medical research, impeding the conduct of large multi-centric studies. Finally, current systems do not help the healthcare provider in making a diagnosis and in determining the medication and health management that is most suited to the individual patient.

This and other advantages of the invention will become apparent on consideration of the ensuing description below.

SUMMARY OF THE INVENTION

The invention is a system and method that automatically initiates a remotely communicated surveillance and health management process to interactively obtain a patient's health-related profile, update and analyze the profiles, categorize the patient's profile by risk-stratification methods using multiple profiles from other patients, and administer a health-related management plan that is relevant to the patient's updated profile and risk-stratification. The invention further provides researchers and healthcare providers to prospectively and retrospectively select patients for study based on data contained within each profile, and each updated profile of each patient.

The invention further provides a system and method to highlight to a patient's provider the patient's condition that require his/her greatest attention using the updated and risk-stratification data obtained by remote iterative and interactive querying of the patient based on updated data from the patient in comparison to updated data from each patient in a study. The invention also assists health care providers in diagnosing and in determining the medication and health management that is most suited to the treatment of each patient, individually, or, in light of risk-stratification analysis, in determining the treatment based upon the risk that a given patent assumes in a group of patients.

In accordance with still further aspects of the invention, the collected data is integrated over multiple healthcare facilities and utilized for the purpose of medical research to enhance the conduct of large multi-center studies.

BRIEF DESCRIPTION OF THE DRAWINGS

The preferred and alternative embodiments of the present invention are described in detail below with reference to the following drawings.

FIG. 6 is a schematic view of an interview form appearing on the screen of the remote terminal of FIG. 1A.

DETAILED DESCRIPTION OF THE PREFERRED EMBODIMENT

Figure 1A:
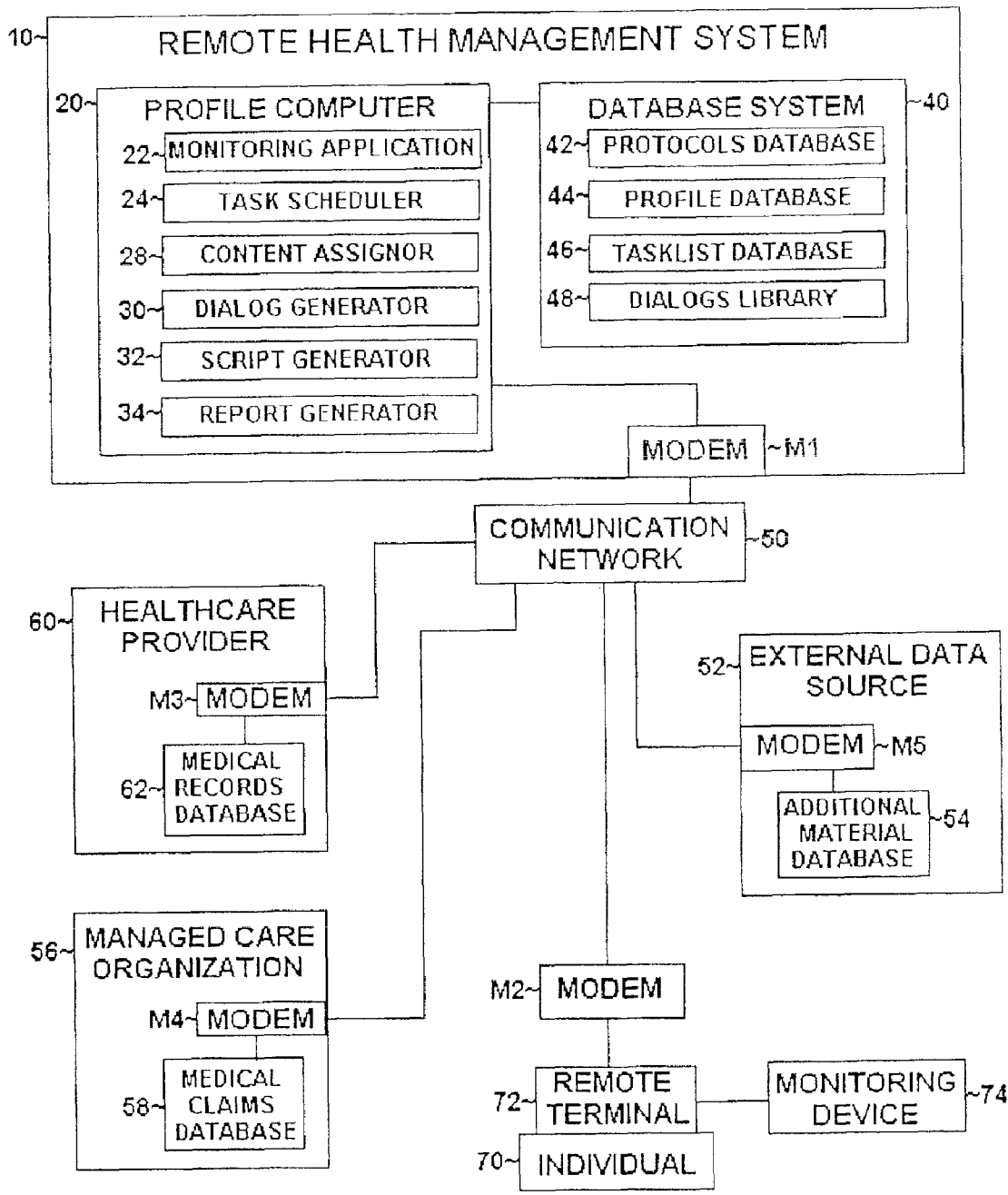
FIG. 1A is a schematic block diagram illustrating the components of the system according to the preferred embodiment of the invention.

Referring to FIG. 1A, the remote health management system 10 includes a profile computer 20 having a monitoring application 22, task scheduler 24, content assignor 28, dialog generator 30, script generator 32 and report generator 34. Profile computer 20 is connected to a database system 40. Database system 40 includes protocols database 42, profile database 44, tasklist database 46 and dialog library 48. Profile computer 20 and database system 40 are networked to a modem M1 for connecting profile computer 20 and database system 40 to a communication network 50.

An individual 70 desiring access to system 10 is located at remote terminal 72. Remote terminal 72 is connected to communication network 50 through a modem M2 such that remote terminal 72 accesses system 10 for interactive health management sessions through modem M2 and communication network 50. It is obvious that many more remote terminals can be connected to communication network 50 for accessing system 10.

A monitoring device 74 for monitoring a health condition of individual 70 is connected to remote terminal 72. Monitoring device 74 is capable of producing measurements of a physical characteristic of the health condition and of uploading the measurements to remote terminal 72 for transmission to system 10. In one possible embodiment, individual 70 is a diabetic and monitoring device 74 is a blood glucose meter for measuring blood glucose levels of individual 70. In another embodiment, individual 70 is asthmatic and monitoring device 74 is a peak flow meter for measuring the individual's peak flow levels. Specific techniques for connecting a monitoring device to a remote terminal for remote monitoring of an individual's health condition are well known in the art.

Communication network 50 further connects a healthcare provider 60 of individual 70 to profile computer 20. Provider 60 has a medical record database 62 for storing electronic medical records of individual 70. Medical record database 62 is connected to communication network 50 through a modem M3 such that profile computer 20 receives through network 50 the stored electronic medical records from database 62. Similarly, communication network 50 connects a managed care organization 56 of individual 70 to profile computer 20. Organization 56 has a medical claims database 58 for storing medical claims data of individual 70. Medical claims database 58 is connected to communication network 50 through a modem M4 such that profile computer 20 receives through network 26 the stored medical claims data from database 58.

Communication network 50 also connects profile computer 20 to an external data source 52 having additional material database 54. Database 54 contains additional dialog libraries, additional protocols and educational materials which may be used to induce a modification in the health related behavior of individual 70. Database 54 is connected to communication network 50 through a modem M5 such that database system 40 may transfer additional educational materials from database 54 to remote terminal 72 through network 50.

It is obvious that a plurality of remote terminals 72 and monitoring devices 74 may be used by the same or different individuals 70 to communicate with remote health management system 10 at any point of time. Further, a given individual 70 may prefer one terminal for data entry, and another for viewing multimedia components, depending on his/her individual taste. For example, an executive with Diabetes may prefer to enter data by the use of a Personal Digital Assistant, but may prefer to receive videos of aerobics on his digital TV at home to help him with his weight reduction program. When this executive is on a business trip, he might wish to answer the queries but skip the digital TV bit. In addition individual 70 may have preferences about the form and manner of presentation of content, including such entities as color, font and background visualization preferences within remote terminal 72.

Further, with the passage of time, newer communication protocols, remote terminals and monitoring devices may become available, and individual 70 may wish to use these newer devices. It would be inefficient for the healthcare provider 60 to create a separate dialog and script for each of the supported device types. Even if this were done, there is the added possibility of the older data being incompatible with the newer systems. To circumvent the above problem, when dialogs 100 that are created by healthcare provider 60 include multimedia and other components as datafiles 136. Script generator 32 reformats these so called 'master-dialogs' into scripts that are interpreted by remote terminal 72 and monitoring device 74.

In the preferred embodiment, communication network 50 is a public communication network such as the Internet, and system 10, remote terminal 72, healthcare provider 60, managed care organization 56, and external data source 52 connect to the public communication network through the use of modems, as illustrated in FIG. 1A. Alternatively, communication network may be a wireless communication network, cellular network, telephone network, or any other network which allows the fore-mentioned devices to exchange data with profile computer 20. For clarity of illustration, only one remote terminal 72 is shown in FIG. 1A. However it is to be understood that remote health management system 10 may include any number of remote terminals, and a single individual 70 may communicate with profile computer 20 through the means of more than one remote terminal 72. Specific techniques for networking computer systems and the electronic devices mentioned above for on-line interaction are well known in the art.

Figure 1B:
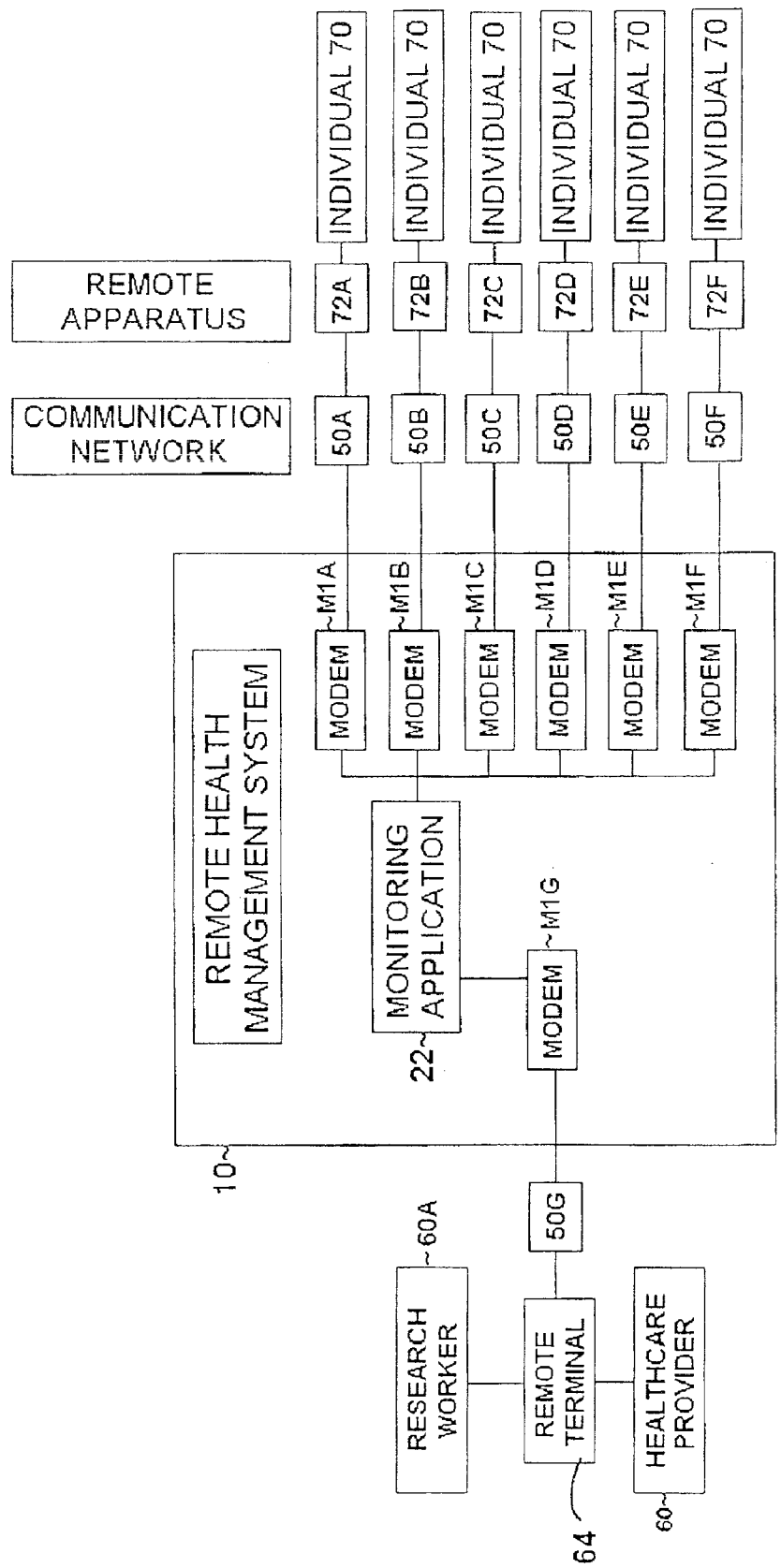
FIG. 1B is a schematic block diagram illustrating the architecture of the system and its connections to multiple individuals at different types of remote terminals according to the invention.

FIG. 1B is a schematic block diagram illustrating the architecture of the system 10 and its connections to multiple individuals at different types of remote terminals according to the invention. Referring to FIG. 1B, multiple individuals 70 use different remote apparatuses 72 (72A, 72B, 72C, 72D, 72E, 72F) in order to receive dialogs and transfer replies and physiological measurements (parameters) to health care provider 60 and research worker 60A, both having access to system 10 via remote terminal 64 in signal communication with network 50G. Network 50G is in signal communication with the monitoring application 22 via modem M1G. Apparatus 72A is preferably a personal computer connected to remote health management system 10 through a high speed internet connection 50A. Here monitoring application 22 connects to modem M1A through a high speed Internet data server (not shown). The advantage of using communication network 50A in delivering content to individual 70 in this instance is that the content presented can be data intensive, including rich graphics and multimedia (video and sounds). Further, the data processing, and storage capabilities of the personal computer may be utilized so that the individual has greater control over the information inputted into the system, as will be described in detail in the alternative embodiment.

Remote apparatus 72B is a handheld mobile communication device such as a wireless enabled personal digital assistant (PDA) or a wireless access protocol (WAP) enabled mobile phone. System 10 communicates with apparatus 72B by a wireless data server and Modem M1B connected to wireless network 50B. An advantage of using apparatus 72B is that individual 70 has greater connectivity when compared with apparatus 72A.

Remote apparatus 72C is a digital television that uses digital television network 50C for data communication. Modem M1C is used in transferring data in the digital television format from monitoring application 22 to the network 50C.

Remote apparatus 72D is a standard dial tone multi-frequency (DTMF) telephone which communicates with system 10 via standard telephone lines. Voice data is routed from monitoring application 22 using a voice data server in system 10 through modem M1D from and to individual 70 via remote apparatus 72D in signal communication with network 50D. Similarly, data received from the individual is used to make changes in the profile. Specific techniques to do this are well known in the art.

Remote apparatus 72E is designed to execute script programs received from the system, and transfer replies and measurements to the system via communication network 50E, that may be an internet connection, standard telephone line, digital television network or a wireless connection in signal communication with modem 1E of System 10. In the preferred embodiment, apparatuses 72A, 72B, 72C, 72D and 72E are directly in connection with system 10. In addition, these apparatuses are connected to at least one remote monitoring device for measuring physiological variables of individual 70. Remote apparatus 72F is a communication enabled monitoring device whereby, connectivity is enabled within the device itself. The enabled monitoring device 72F uses network 50F that may use the internet, standard DTMF telephone line, wireless network or a digital television network to communicate with system 10. An advantage of using the enabled device 72F is reduced cost of the entire unit for the individual.

Healthcare provider 60 utilizes a remote terminal 50G in order to access patient profile databases, requisition reports, and to manually assign script programs to the individuals, either singly, or to an entire group of patients. Further the system may be also be used to schedule consultations and fix appointments with the individual monitored patient. Remote terminal 50G is preferably a workstation connected to the system using a secure internet connection. Further, any person desirous of communicating with individuals 70 may be additionally granted access to the system using the remote terminal (workstation) 50G. This may include an administrator who wishes to enroll patients, collect, analyze and report data. Further, a researcher who wishes to enroll patients for the purpose of research, or who wishes to access the data within the profile database may additionally be granted access to the system.

In the preferred embodiment, the components of system 10, such as monitoring application 22, task scheduler 24, dialog generator 30, script generator 32, profile database 44 and tasklist database 46 are all physically located within the profile computer 20 and database system 40. In an alternative embodiment, the remote apparatus additionally includes one or more components that are contained within the profile computer in the preferred embodiment. In one instance, the individual's profile database 44 may be stored, at least in part within the remote apparatus itself. The profile database 44 on the remote apparatus is synchronized with that on the database system 40. An individual would not need to establish a connection with the profile computer every time he/she wishes to enter data into the system. This is particularly advantageous where the individual has to reply to the same or similar queries over a period of time. For example, a patient undergoing treatment for mood disorders may be asked to maintain an electronic 'diary' where he/she answers queries regarding his/her mood. In the alternative embodiment, data entered each day would be used to build the patient's profile database. At the end of a period of time, the apparatus would transfer the newly added profile variables and this information would be used to update the individual's profile. Alternatively, the electronic 'diary' may also be presented to the healthcare provider at a personal visit.

The profile database also includes information regarding the individual's preferred media, personal preferences, and visualization options. Henceforth, in instances where mass media modalities such as digital television are used for communication, the program logic may be broadcasted to all the individuals, and a personalized experience may be created through local processing and locally stored profile variables The monitoring application and components of the protocols database may additionally be incorporated within the remote apparatus. The monitoring application within the remote apparatus scans the profile database for 'suspicious' correlates of data, as defined in the protocols database. If at any time, a combination of variables in the profile database is suggestive of an acute crisis or a worsening disease state, then the monitoring application is activated, and this establishes a connection with the profile computer. At regular intervals of time, the profile database, protocols database are updated for newer information and protocols.

The alternative embodiment has the advantage of lowering the communication costs with the system. A further advantage with the alternative embodiment is that the individual exercises greater control over the data that he/she wishes to provide to the system, which is preferable to many individuals.

Figure 2:
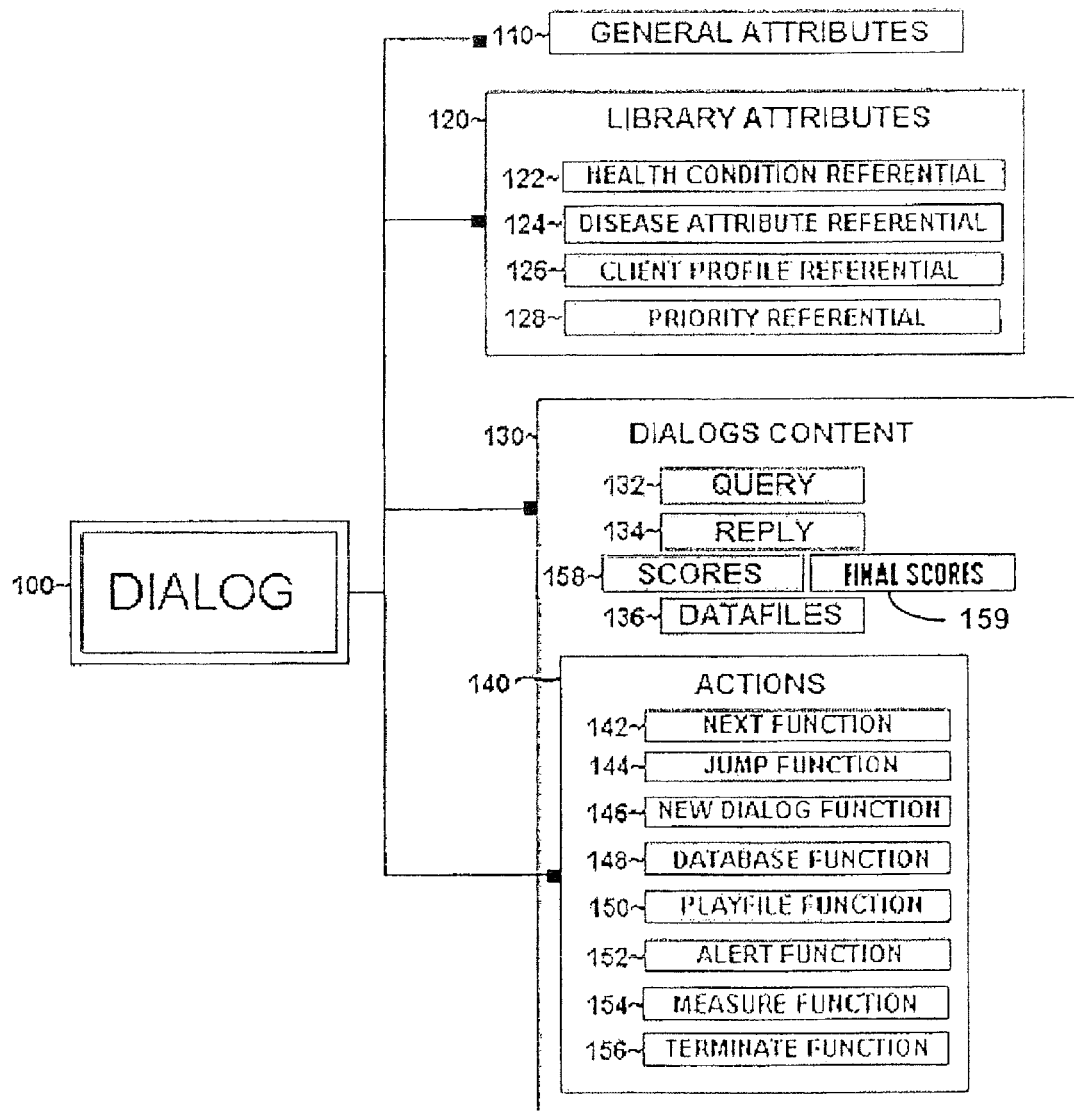
FIG. 2 is a block diagram depicting interdependent characteristics (operators) of a dialog.

FIG. 2 is a block diagram depicting the interdependent characteristics (operators) of a dialog 100 in the system matrix. The interdependent characteristics include the dialog's general attributes 110, library attributes 120 for the aspect of care addressed and dialog content 130, the active content of dialog 100. Dialog attributes 110 define such characteristics of the dialogs such as the name of the dialog, the unique code that is used by the system to refer to the dialog, version of the dialog, the name of the dialog creator, the date of creation and last update of the dialog. Dialog attributes 10 further includes information regarding the previous versions of the dialog, and references to those dialogs that are derivatives of the current dialog, besides containing a reference to the previous versions of the dialog.

Library attributes 120 of a dialog include those attributes that define the place of the dialog in the library. Besides allowing for the searching, updating, and classification and retrieval of dialogs by healthcare provider 60, the information contained within library attributes 120 is also referenced by content assignor 28 in order to assign a particular dialog to the individual 70 from amongst the plurality of dialogs within the library of dialogs. Library attributes 120 includes a health condition referential 122, disease attribute referential 124, client profile referential 126, and a priority referential 128.

Health condition referential 122 includes information on the disease state or health related condition and attribute in the management of which the dialog would typically need to be employed. The states that are defined by health condition referential 122 are not necessarily exclusive and can often overlap, and be subsets of other health condition referentials particularly so when the disease or health related condition is present in a diverse population. For instance there may be one attribute that relate to diabetes, and another that relates specifically to juvenile diabetes (a form of diabetes). Obviously, dialogs containing health condition referential 122 that relate to diabetes can be freely applied to all patients who have juvenile diabetes but not vice versa. An advantage of the above is that it decreases the number of dialogs that have to be created for managing conditions that present in a diverse population.

Disease attribute referential 124 declares a specific attribute of the disease or health related condition that relates to the said dialog 100. Disease attribute referential 124 in a disease such as diabetes may include references to organs that are damaged as a result of the disease in the longer term as a result of poor glucose control, such as that for the kidneys, the blood vessels, the eyes and the feet, to name a few. It can further include follow up material that relates to patient's compliance with medication, patient's compliance with dietary modification, a weight reduction program, and a module that ensures that the patient is monitoring his/her blood sugar regularly. Thus, diseases and health related states are divided into a plurality of attributes, and these attributes are referenced in the disease attribute referential 124.

Patients (individual 70) may vary widely in their educational background, comprehension capacity, motivational drivers, attitude and perception of their condition, and preference of communication medium. In order to communicate well with the patient, it becomes necessary to optimize the communication to one that is best suited to a particular patient. Client profile referential 126 defines the characteristics of individual 70 in whom the particular dialog 100 would likely be effective and pertinent. Thus, at the time of assignment of a particular dialog 100 to individual 70, either by the automatic content assignor 70 or by healthcare provider 60, it is ensured that dialog 100 is individualized to the patient not only in terms of the disease condition or requirement in the patient's health condition, but also in terms of the patient's individual preferences.

Priority referential 128 describes the relative importance of the dialog in terms of urgency, value of the particular information in the management of the health related condition and health attribute status of individual 70. Priority referential 128 includes information that enables the system to prioritize from among a set of possible dialogs that would need to be served on individual 70. Further, priority referential 128 defines the sequence in which dialog 100 appears in a particular communication.

Dialog content 130 further includes queries 132, replies 134, datafiles 136 and actions 140. Query 130 may be a question statement to a patient regarding a particular aspect of the disease or health related condition. Text markers at the beginning of a particular query are used to identify a given query 132 within dialog 100. Each query 132 is followed by a list of possible replies 134, and the patient is asked to select the best reply 134. Of course, it is possible that, in the case of some queries 130, more than one reply is possible. In such a case, the patient is asked to choose all the replies 134 that apply. Actions 140 define the next step to be followed for each of the possible replies. Of course, when more than one reply 134 is allowed for a particular query 132, actions 140 would define the procedure to be followed for each of the possible allowed combinations. Alternatively, default actions 140 may be assigned within a dialog 100 for that reply 134 to which no action 140 has been defined. For instance, one such default action would be to go to the next query. Further, more than one action 140 may be assigned to a particular reply 134.

Possible actions 140 includes next function 142, jump function 144, newdialog function 146, database function 148, playfile function 150, alert function 152, measure function 154 and terminate function 156. When Next function 142 is applied to a particular reply 134, the next query is put to the user. Jump function 144 instructs the program to go to specified query 134 within dialog 100. Newdialog function 146 instructs the program to terminate the present dialog and download another dialog 100 from communication network 50 or that stored at remote terminal 72. Database function 148 instructs the program to make amendments and additions in profile database 44 and tasklist database 46. Playfile function 150 instructs the program to download and run a specified datafile 136 from communication network 50 or that stored at remote terminal 72. It is of particular value where multimedia components such as digital audio and video streams containing health related messages may be played to individual 70.

Alert function 152 instructs the program to send an alert message to healthcare provider 60 informing him/her of the receipt of specified reply 134 to query 132. Alert function is intended to be used in case a given combination of replies received from individual 70 is likely to lead to a poor health status in the near future, and/or when immediate intervention is required and/or the healthcare provider 60 would need to be informed about the reply 134 urgently. Measure function 154 contains instructions to remote terminal 72 to collect measurements from monitoring device 74. Health related parameters may be collected from individual 70 and sent to remote health management system 10 by this function.

Terminate function 156 instructs the program to terminate the execution of specified content 130. Terminate function 156 additionally includes an arithmetic or logical method for computation of the results of a specified group of queries 132 and replies 134. For example, dialog content 130 can include a number of queries, with each of the replies being assigned a score 158. Terminate function 156 may be used to instrict the program to compute arithmetically the final score 159 for a given set of queries 134. Alternatively, logical methods may be used to derive score 159 for each of one or more combinations of replies 134. Alternatively, any of actions 140 may be assigned to final score 159. An advantage of terminate function is that long standardized questionnaires for risk determination in a variety of conditions may be applied to individual 70 in their original format and scored automatically, and the final score 159 be further used to execute action 140. It will be obvious to anyone versed in the art that a number of methods and programming languages are available to write programs that can interpret dialog content 130 and perform any of the above functions.

Figure 3:
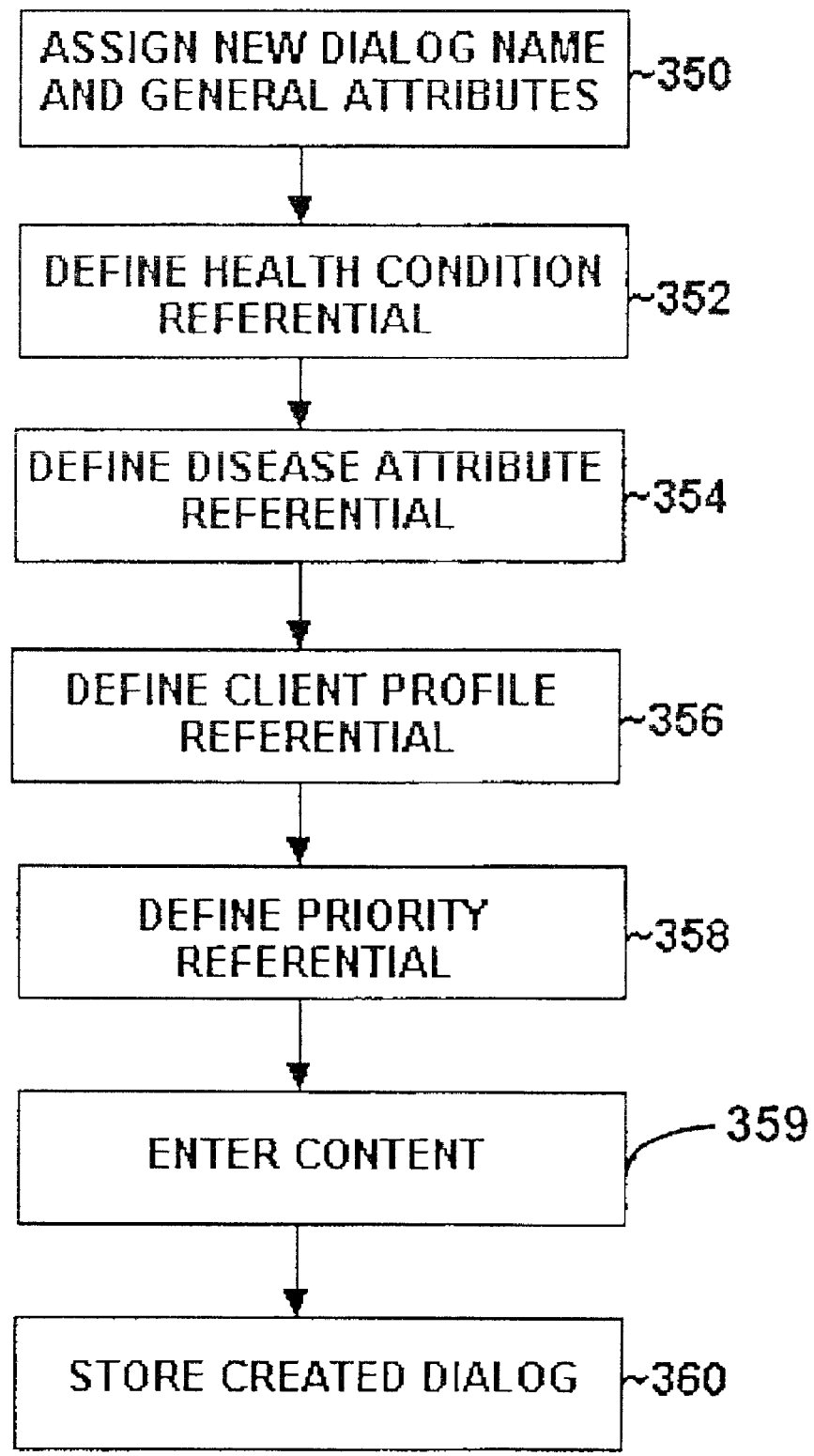
FIG. 3 is flow chart depicting the steps in creating and storing of content data from a dialog.

FIG. 3 is a flow chart depicting the steps in creating and storing of dialogs 100. A healthcare provider's first task is to assign a name, and provide the general attributes of the dialog-to-be-created as depicted in block 350. Next, the user defines the health condition to which the dialog will primarily refer (health condition referential 122) at block 352. The provider then identifies an aspect of care at block 354 to which the dialog will primarily refer (disease attribute referential 124). Following this, the provider identifies the profile of the individuals to whom the dialog is customized (client profile referential 126) in block 356, and the priority given to the dialog and the health context that it attempt to modify (priority referential 128) in block 358. Once the naming conventions and the attributes of the dialog 100 are assigned, the provider creates dialog programming statements at block 359, in a graphical programming environment as embodied in FIG. 4. New dialog content is then stored in the dialog library 48 at block 360.

Figure 4:
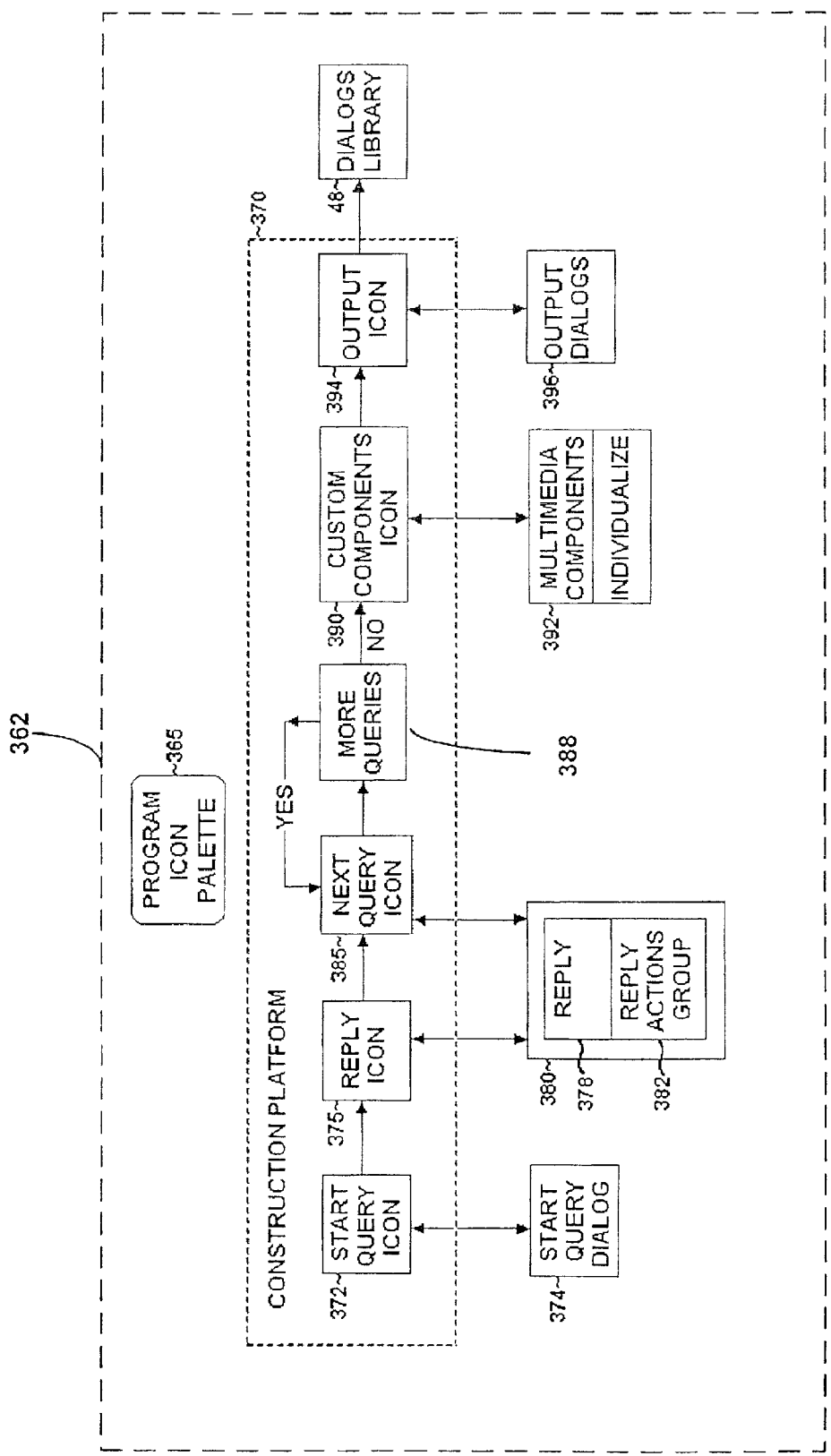
FIG. 4 is a flow chart diagram depicting the creation of the programming statements using a Dialog Editor Platform.

The provider who has access to create new content does so using a simple dialog composer as embodied in FIG. 4. FIG. 4 is a diagram depicting the creation components of a dialog Editor Platform 362. First, a provider is presented with a program icon palette 365 of programming statements that are represented as graphic symbols (icons) that can be dragged from the palette of available statements into a dialog construction platform 370. In a typical embodiment of the present invention, the provider drags a start query icon 372 and a multi-pronged reply icon 375 from an icon palette down to the construction platform 370. The provider then activates a dialog box for each icon by clicking on it with a mouse and specifying a query associated with that particular icon, for example, a Start Query Dialog 374. Next, in a Reply Dialog 380, the provider assigns one or more actions 140 of reply action group 382 to each reply 378. The reply actions group 382 includes one or more actions 140 i.e. the execution of an arithmetic function on risk value R, and/or appending/modification of data within database system 40, execution of follow up queries, playing multimedia files on remote terminal 72 and collecting measurements from monitoring device 74. In those actions 140 which have pointers to follow up queries, next query icon 385 is dragged onto the construction platform along with an associated reply icon 375, in the same manner as described for reply icon 375.

The same steps 388 are repeated for each of the follow up queries, till all the queries and follow up queries within the dialog 100 have associated actions 140 assigned to them. By clicking on customization icon 390, the provider activates customization dialog box 392. Customization dialog box 392 allows the user to customize the dialog to different kinds of remote terminals 72 and monitoring devices 74, and make additions to the output over and above the baseline dialog. For instance, the provider can include specific multimedia components to be served on individual 70 in addition to/lieu of any of the actions 140 wherever the remote terminal 72, monitoring device 74 and communication network 50 support it. The advantage of customization dialog box is that it allows the provider to make additions to existing dialogs and add multimedia and other components without changing the basic structure of the queries that are applied to individual 70. In this manner, a 'master dialog' can be initially created that includes data components of all supported remote terminals 72. As and when newer and enhanced versions of remote terminals 72 become available, the corresponding components may be selectively appended and modified within dialog 100.

By clicking on the output icon 394, the provider activates the output dialog box 396. At any time during or after the dialog creation process, the provider can review the dialog created, using a simulation interface to an appropriate appliance, or alternatively the provider can review the actual dialog content in a text only overview window.

Once all the follow up queries, replies and output dialogs are formulated and put onto the construction platform 370, the newly created dialogs are stored in a dialogs library 48 from where it may be incorporated by provider 60 and content assignor 28 in care management programs and for future updating and editing.

Figure 5:
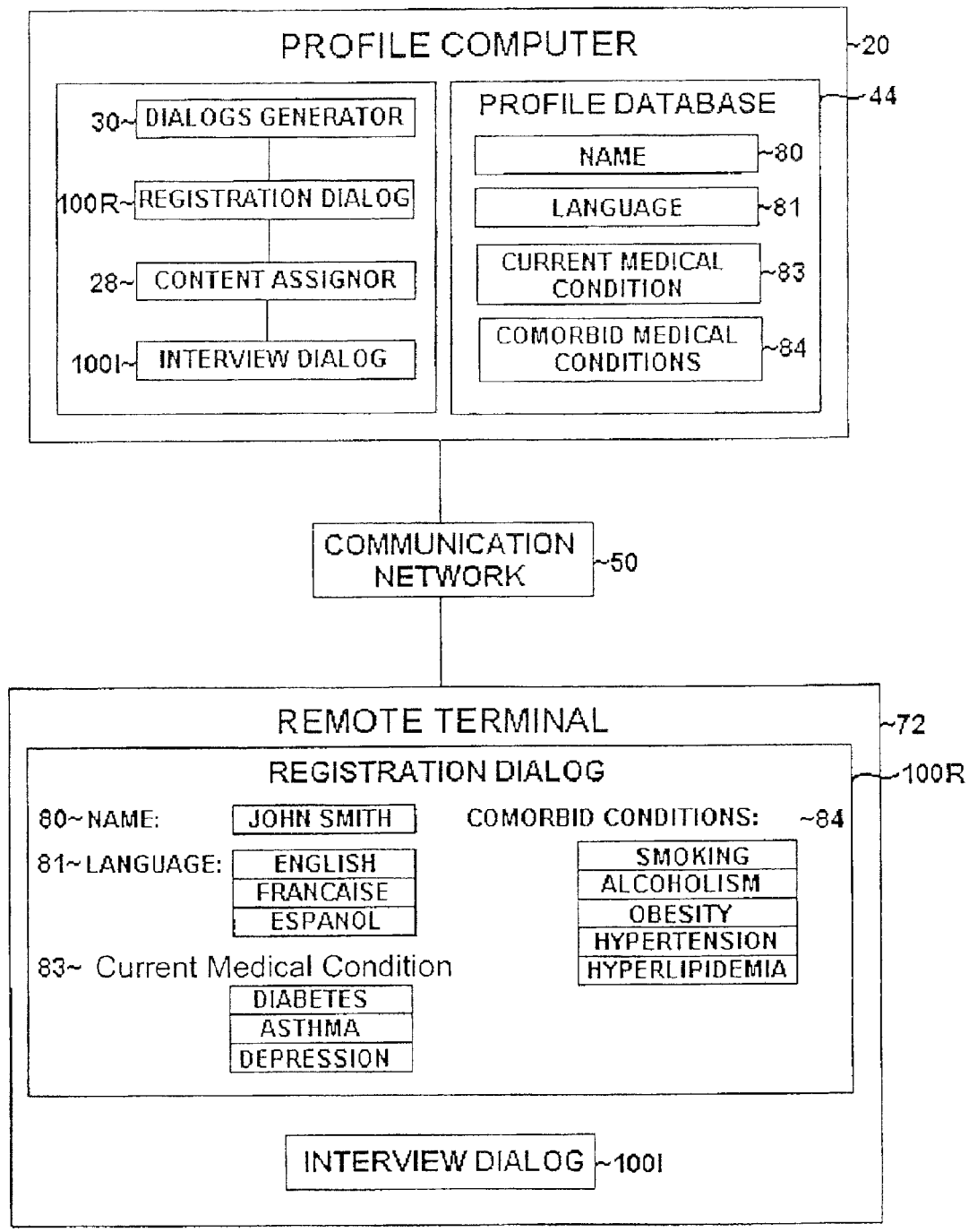
FIG. 5 is a schematic block diagram illustrating the generation of an interview form according to the method of the invention.

Referring to FIG. 5, the profile computer 20 includes the dialog generator 30 and is capable of generating an interactive dialog 100 and of transferring it through communication network 50 to the display unit of remote terminal 72. At the time of initial registration of individual 70 in the system, dialog generator 30 generates a registration dialog 100R and transfers it through communication network 50 to remote terminal 72. Registration dialog 100R includes data fields for a name 80, a language 81, current medical condition 83, and co-morbid health condition 84 of individual 70. Profile database 44 has storage capability for storing profile record 45 that includes, name 80A, language 81A, current health condition 83A and co-morbid health condition 84A of individual 70.

In the preferred embodiment, dialog library 48 stores hundreds of dialogs 100 in various languages relating to possible health conditions of individual 70, such as asthma, diabetes, nicotine addiction, etc. To narrow the focus of registration dialog 100R, dialog generator 30 communicates with content assignor 28, which tailors an interview dialog 100I in dependence upon language 81 and current and co-morbid health conditions of individual 70. For example, in FIG. 5, individual 70 has indicated his language 81 as "ENGLISH" current medical condition as "DIABETES" and co-morbid health condition 84 as "SMOKER" so content assignor 28 assigns interview dialogs 100I that contain English language queries pertaining to diabetes and smoking related behaviors of individual 70. As illustrated in FIG. 5, language 81 further includes French and Spanish. Other languages may be included. Current medical condition 83 also includes asthma and depression. Other medical conditions may be included. Co-morbid condition 84 also includes alcoholism, obesity, hypertension, and hyperlipidemia. In an alternative embodiment, content assignor 28 uses data from medical records database 62, medical claims database 58, and/or additional material 54 to assign registration dialog 100R individual 70.

Registration dialog 100R is illustrated in greater detail in FIG. 6. Registration dialog 100R contains a first category of queries 160 relating to the current health condition of individual 70. Category 162 is divided into a first subset of queries 162 for determining current diseases or symptoms of individual 70 and a second subset of queries 164 for determining the pattern and history data of the individual's health condition. For example, in the example in which individual 70 is a smoker, subset 162 asks about any current diseases or symptoms smoking has caused in individual 70. Similarly, subset 162 asks for the pattern and history data of the individual's smoking habit.

Registration dialog 100R further includes a second category of queries 166 for determining the motivational drivers of individual 70. Category 166 is divided into six subsets of queries including longevity 168, quality of life 170, family life 172, social responsibility 174, social acceptability 175 and economy 176 for determining a value placed by individual 70 on various motivating factors for modifying his or her behavior. Subset 168 is for determining the value placed by individual 70 on longevity. For example, where individual 70 is a smoker, subset 168 includes queries to determine if the prospect of living a long life would provide sufficient motivation to quit smoking.

Subset 170 is for determining the value placed by individual 70 on the quality of his or her life. In the smoking example, subset 170 includes queries to determine if an improvement in smoking symptoms, such as no longer suffering coughing fits, would provide sufficient motivation to quit smoking. Subset 172 is for determining the value placed by individual 70 on family life. In the smoking example, subset 172 includes queries to determine if an improvement in family life, such as no longer harming relatives with second hand smoke, would provide sufficient motivation to stop smoking. Subset 175 is for determining the value placed by individual 70 on social acceptability. In the smoking example, subset 175 includes queries to determine if an improvement in social acceptability, such as no longer offending people with bad breath, would provide sufficient motivation to quit smoking.

Subset 174 is for determining the value placed by individual 70 on social responsibility. In the smoking example, subset 174 includes queries to determine if an improvement in social responsibility, such as not burdening society with the cost of Emphysema treatment, would positively motivate individual 174 to quit smoking. Subset 176 is for determining the value placed by individual 70 on economy. In the smoking example, subset 176 includes queries to determine if the cost savings associated with no longer purchasing cigarettes would provide sufficient motivation to quit smoking.

Registration dialog 100R also includes a third category of queries 178 for determining the comprehension capacity of individual 70. Category 178 is divided into four subsets of queries including age 180, language skills 182, reading habits 184, and educational background 186 for determining various comprehension capacity factors. Subset 180 is for determining an age of individual 70 and subset 182 is for determining language skills of individual 70. Similarly, subset 184 is for determining reading habits of individual 70 and subset 186 is for determining the educational background of individual 70.

A fourth category of queries 188 is for determining a media preference of individual 70. Category 188 is divided into three subsets of queries including picture 190, text 192 and video games 194 for determining if the individual 70 prefers pictures, text, or video games, respectively. Of course, these types of media are just examples of possible media choices and other media, including mixed media selections, are possible in alternative embodiments. Registration dialog 100R and educational fulfillment bank 22 may offer other media choices in alternative embodiments, such as computer videos, musical lyrics, or hyper-text links.

Figure 7:
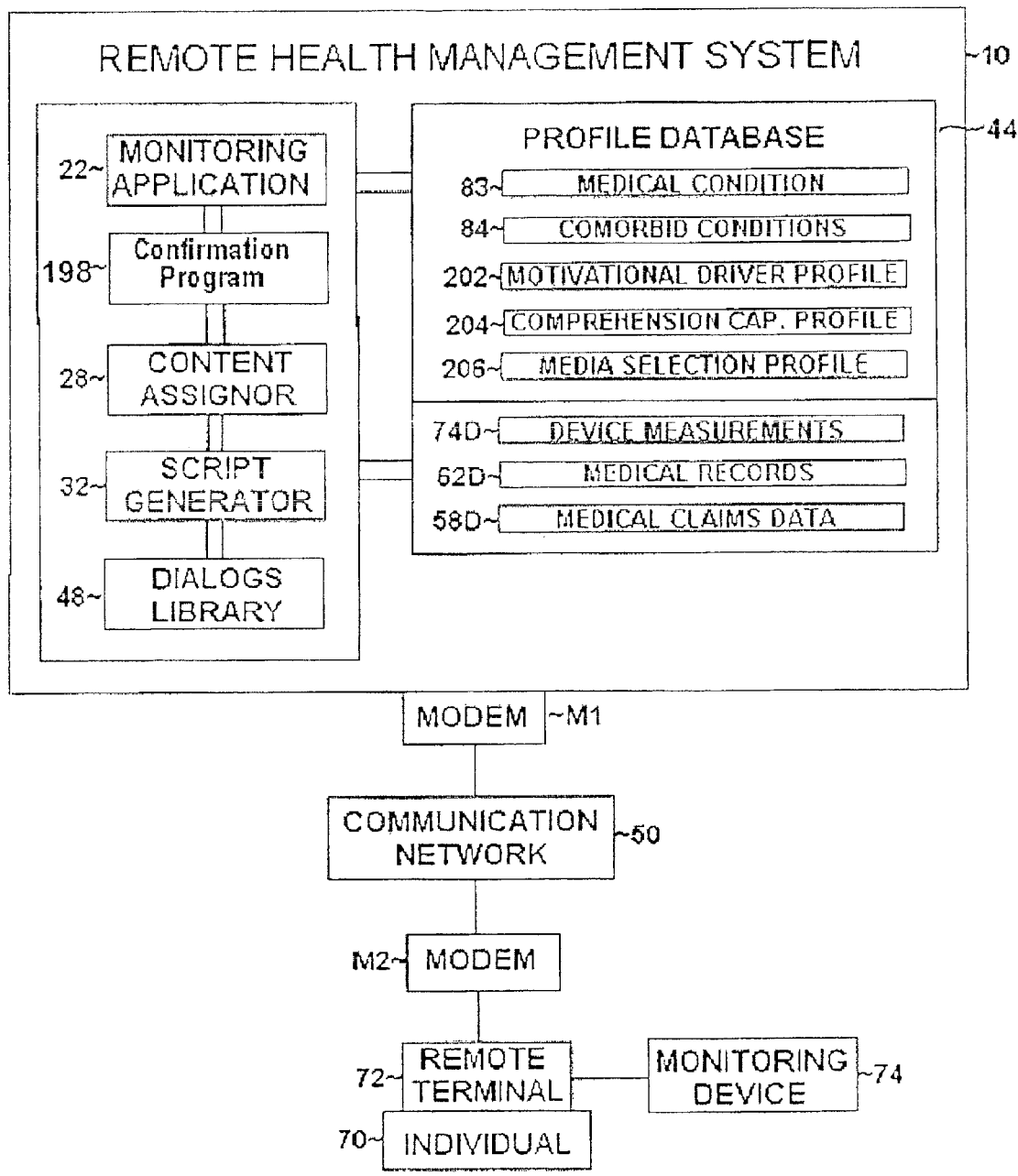
FIG. 7 is a schematic block diagram illustrating the functions of individual component programs at the profile computer of the remote health management system.

Referring to FIG. 7, monitoring application 22 is designed to generate a profile database 44 that includes a motivational driver profile 202, a comprehension capacity profile 204, and a media selection profile 206 from the questionnaire replies. Monitoring application 22 further includes a confirmation program for sending a confirmation form 198 to remote terminal 38. The confirmation form includes a summary of each generated profile 202, 204, and 206 so that individual 70 may confirm each of the generated profiles. Profile database 44 is also designed to store a profile record of individual 70 including his or her name, current health condition, and confirmed profiles. Additionally, profile database 44 includes medical claims data 58D received from claims database 58, electronic medical records 62D received from medical record database 62, and device measurements 74D received from monitoring device 74. Thus, profile database 44 includes representing the medical condition 83 of individual 70, co-morbid health conditions 84, health related parameters, and progress regarding the conditions.

Content assignor 28 is designed to parse through data contained within profile database 44, and selects those dialogs 100 from profile database 44 that are most appropriate to the health condition, profile, and needs of individual 70. The selected dialog(s) 100 are exported to script generator 32 that individualizes the dialog to individual 70, stores it in the dialogs library 48, and converts it to a format that is recognized by remote terminal 72 and sends it over communication network 50 via modem M1. The communication network 50 exchanges data between the monitoring device 74 and the individual 70 through the remote terminal 72 and the modem M2.

Figure 8:
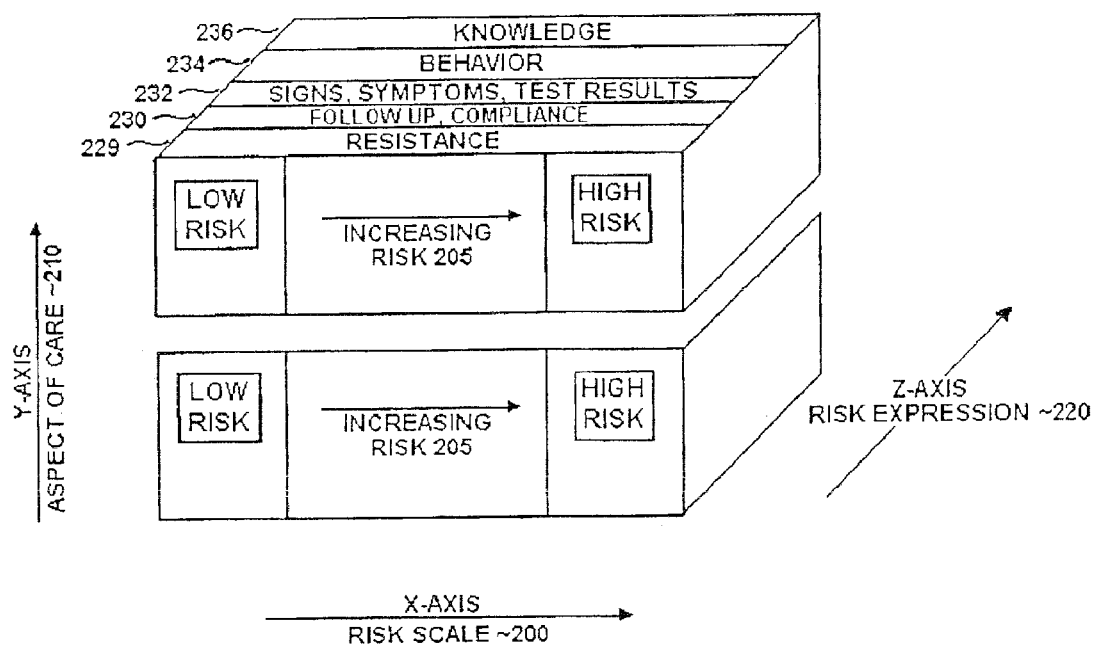
FIG. 8 is a block diagram illustrating the three dimensional aspects of the dynamically determined risk state output scale.

FIG. 8 is a block diagram illustrating the three dimensional aspects of the dynamically determined risk state output scale which is subsequently used by content assignor 28 to determine the most appropriate dialogs 100 for assignation to individual 70. The X-axis 200 defines the relative risk of individual 70 on an arbitrary relative scale. Replies 134 to query dialogs 132 sets the risk score 205 at a certain level on the scale, and further replies 134 may be used to modify the assigned score 205 in either direction. Actions 140 of dialog content 130 may so be programmed that the new risk score 205 is a value derived from arithmetic modification of the risk score 205 that was assigned previously to a specified parameter in the risk profile of individual 70. Over a period of time, replies 134 can lead to the creation of an accumulated risk profile. Additionally, replies 134 to dialogs 100 that are incorporated as a value in a mathematically calculated risk state may incorporate other answers as well, creating a composite, weighted risk state. The Y-axis 210 refers to the actual aspect of care in which the risk will be incorporated. The Z-axis 220 incorporates the expression of risk, i.e., whether the risk is assigned to a sign or symptom 232, a behavior 234, or a knowledge expression 236. An individual 70 on follow tip for long periods may additionally be assigned follow-up risk 230 that compares the health related parameters, compliance to medication etc over a long period of time, and charts the course of the health related parameters of individual 70. Similarly, the individual 70 on follow up for long periods may additionally be assigned follow-up resistance risk 229 that compares the health related parameters, resistance to medication etc over a long period of time, and charts the course of the health related parameters of individual 70. This dynamic model allows for very sophisticated risk profiling including risk trend alerts, composite risk profiling by aspects of care and profiling by risk expression, as will be described in the charts below. Further, the dynamic risk 'foot prints', or the pattern of risk scores 205 at any time can serve as triggers for automated content selection.

While a considerable amount of health related data may be available regarding an individual 70, in the interest of the health provider's productivity, it is pertinent that only relevant data is presented. It is also preferable that the healthcare provider 60 views patients with similar health status as a group, and decides the future plan of management accordingly. Report generator 34, and report generator interface 300 are used to generate reports which are used by healthcare provider 60 in following the health status of individuals 70 or groups of individual 70.

Figure 9:
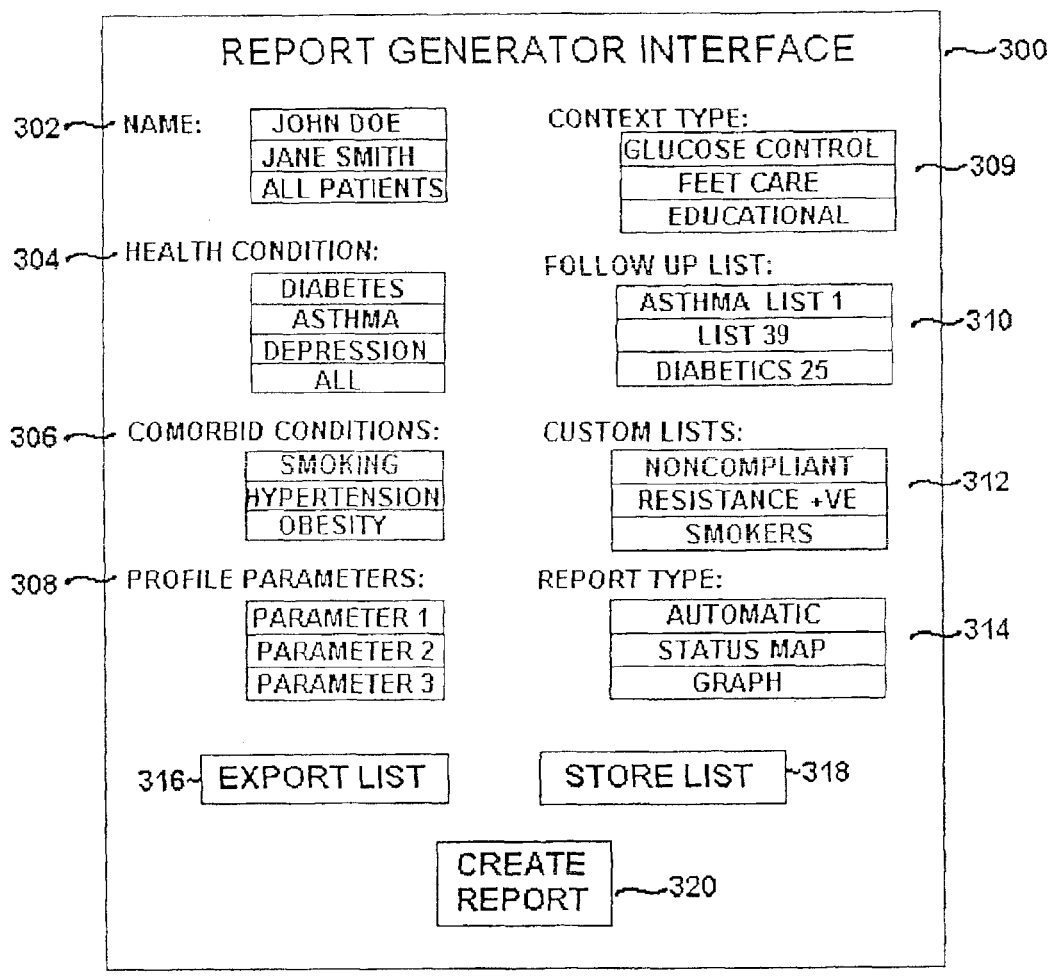
FIG. 9 is a schematic view of the report generator interface, as it appears to the healthcare provider.

FIG. 9 shows the report generator interface 300 as viewed by healthcare provider 60. It includes fields Name 302, health condition 304, co-morbid condition 306, profile parameters 308, context type 309, follow up list 310, custom list 312, report type 314, export list button 316, store list button 318 and create report button 320. Name 302 is a drop-down menu that includes the names of all individual 70 that are managed by healthcare provider 60. Healthcare provider 60 has the option of selecting one or more individuals 70 from the drop down menu, for whom he/she wishes to view a generated report 320. Health condition 304 is also a drop-down menu with a list of all the medical conditions 83 which provider 60 is managing. Similarly, co-morbid condition 306 includes all the co-morbid conditions that are seen in individuals 70.

Profile parameters 308 allows healthcare provider 60 to select individual 70 by any aspect of data available in their profile database 44. Examples of this include can include (1)

individuals 70 who use digital TV as their remote terminal 72, (2) individuals with diabetes with poor sugar control scores, (3) individuals who are showing resistance to smoking cessation messages, (4) individuals who have not entered data into the system for more than 3 continuous days, (5) individuals with mood disorders who have refused to answer queries regarding illicit drug abuse, (6) individuals with risk scores below a predetermined level in any context, etc. It will be appreciated that possible profile parameters 308 that healthcare provider 60 can create or select are limitless, and that the examples illustrated above are only broadly indicative of the many parameters available to healthcare provider 60. In addition, it is also possible for healthcare provider 60 to select a combination of two or more parameters, for the purpose of analysis, and report generation.

Context type 309 is another drop down menu that allows healthcare provider 60 to choose from one or more contexts or attributes within health conditions 304 and co-morbid conditions 306.

Store list button 318 allows healthcare provider 60 to store the actual list of names for future recall and use for later reference at follow up list 310. Similarly custom list 312 allows healthcare provider 60 to store the parameters that are used to create the list, for future reference and follow up. Export list button 316 allows healthcare provider 60 to send the list to other programs within system 10, including monitoring application 22, task scheduler 24 and content assignor 28. Export list 316 may be used to assign specific dialogs 100 to individuals 70 by directly using the report generator interface. Additionally, specific tasks may be queued within the task scheduler 24 in order to execute them (such as delivering a dialog) at a later date. Custom list 312 may be exported to monitoring application 22 to create a new protocol, in order that all future individuals 70 fulfilling the said criteria are automatically assigned the specified dialog 100, or action 140.

Report type 314 menu allows healthcare provider 60 to chose from among a set of available types of reports. Different types of reports are suited to depicting different aspects of information about the patients and group of patients. One possible report type is a risk map, whereby the risk factors of selected individuals 70 are depicted as a status map on the basis of their computed health risk. Another possible report type is a temporal graph, whereby lines are drawn showing the temporal progression of the computed risk in one or more contexts. Color coding may be used to depict different patients and contexts separately. A third possible report type is one where individuals who are most in need of medical attention are selectively listed by priority, urgency, name or any parameter within database 40, using arithmetically computed risk factor variables. A fourth type of report is a detailed patient report where all the relevant parameters within the database is listed, alongside the analysis reports of the content assignor, and the rationale behind the automated script assignment.

Figure 10A:
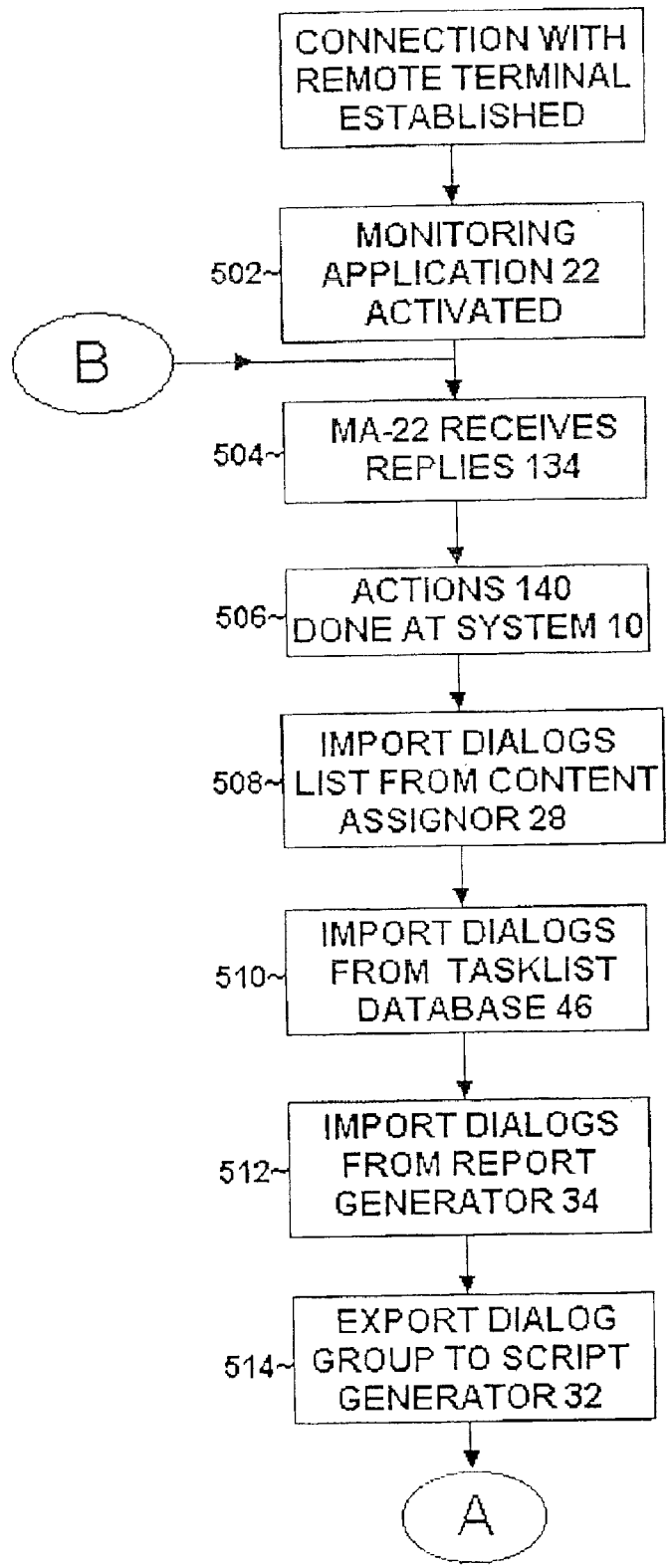
FIG. 10A is a flow chart illustrating steps included in the method of the invention.
Figure 10B:
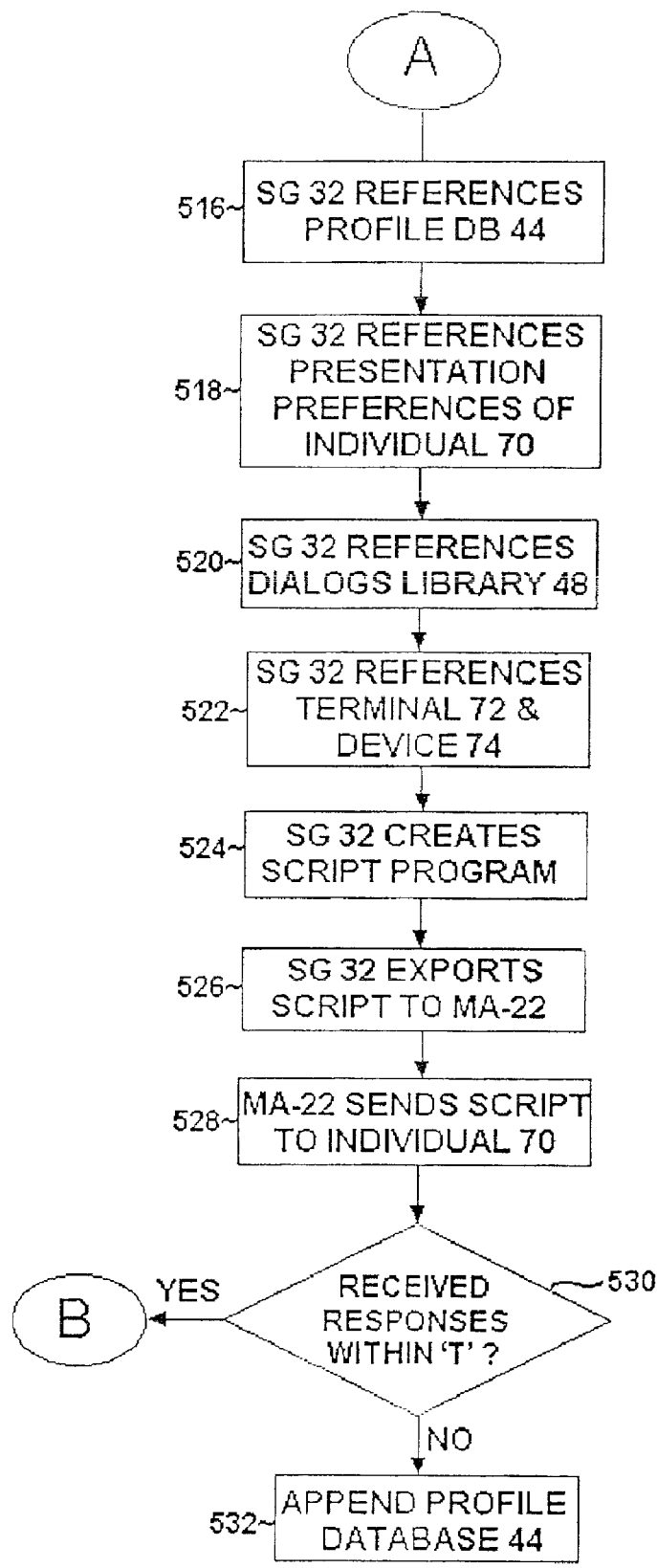
FIG. 10B is a continuation of the flow chart of FIG. 10A.

FIG. 10A is a flowchart providing an overview of the various steps involved in the system-individual interaction, described from the level of remote health management system 10. FIG. 10B is a continuation of the flow chart of FIG. 10A.

In step 502, monitoring application 22 is activated after the establishment of a successful connection with remote terminal 72. In step 504, replies 134 are received to previously sent dialogs. In step 506, actions 140 are performed at the level of the system on the basis of received replies 134. These actions include amending the profile database 44, adding new tasks to tasklist database 46, and serving new dialogs 100 to individual 70. In step 508, content assignor 28 scans profile database 44, and assigns dialogs 100 to individual 70 in the order of decreasing importance in health management. In step 510, an additional list of dialogs 100 is received from tasklist database 46. In step 512, healthcare provider 60 may additionally use report generator 34 to add dialogs 100 to that from steps 508 and 510. Alternatively, healthcare provider 60 may add dialogs 100 to the tasklist database 46, which are sent to individual 70 at a future time.

In step 514, monitoring application 22 groups the dialogs into a logical sequence and exports an ordered and often truncated list to script generator 32. In step 516, script generator 32 references profile database 44 to elicit information on the type of remote terminal 72, monitoring device 74, and communication network 50 that will be used to communicate with individual 70. Additionally the visualization and content presentation preferences of individual 70 are referenced in step 518. In step 520, script generator 32 references dialog library 48 and elicits relevant dialog content 130 (including datafiles 136) that is compatible with communication network 50, remote terminal 72 and monitoring device 74.

In step 522, script generator 32 may additionally communicate directly with remote terminal 72 and monitoring device 74 to elicit the characteristics of the devices and stored individual preferences, and parameters within, in order to customize the script. In step 524, script generator 32 creates a customized program. Finally, in step 526, script generator 32 exports the customized script program to monitoring application 22.

In step 528, monitoring application 22 sends the script program to individual 70 via communication network 50. Monitoring application 22 waits until a specified time 'T', typically between 24 to 48 hours, for individual 70 to respond to the script program (step 530). In case responses are received, the application continues along step 504. Alternatively, if replies are not received within time 'T', monitoring application adds information regarding the non-receipt of replies to profile database 44 (step 532). This information may be accessed and used separately by report generator 34, task scheduler 24 and content assignor 28.

Content Assignment and Data Analysis Methods

The system works on the following premise: since each of the patients managed by the system has an individualized treatment protocol which is based on the unique health related parameters of the patient, ideally each patient must also be followed on an individual basis by the healthcare provider. However, this approach is inefficient in that it would require the health provider to spend considerable time following those patients who otherwise present little risk as far as compliance with medical advice is concerned. In addition, these patients are usually well motivated and likely to follow medical advice, and the management would primarily consist of confirming and maintaining their low-risk status.

On the other end of the spectrum is the other group of patients who are less motivated to look after themselves, and less likely to modify their disease related behaviors on their own accord, and without continued encouragement and support from the healthcare system. These patients need regular monitoring of their health related parameters, sensitization to the need to modify disease related behaviors, continued psychological support, health education and encouragement to comply with prescribed treatment regimens in order to prevent their disease condition from worsening. This group of patients is responsible for a greater proportion of total morbidity and mortality from chronic illnesses than the rest of the population.

The method of managing patients varies significantly between the two groups of patients. While the first group may be managed by assigning content that is dynamic and individualized to the patient profile automatically, the second group requires more active participation and involvement of the provider in the management process. In this second group, the provider would need to probe deeper and develop novel strategies in order to treat the individual's condition.

The two groups are, however not mutually exclusive. Some patients who are initially poor risks may be gradually motivated and encouraged so that they acquire the low risk status of the first group. Likewise, it is also necessary to ensure that patients belonging to the first group continue participating actively, and remain involved in the upkeep of their own health, so that they do not acquire the risk profile of the second group.

Stated simply, the system consists of a consists of a patient profile, which contains details of the patient's condition, and details of co-existing conditions (co-morbid conditions) that may have a bearing on the way the patient is managed by system 10. These details are expressed in the form of Risk factors (R) that numerically depict the level or state of risk a patient is in, for each of the numerous aspects of disease (context).

The profile may be formed on the basis of an initial dialog (registration dialog 100R). In addition, profile data may be derived from information contained within the patient's medical records database (clinician's notes), claims database (from the patient's insurer, employer, managed care organization, care provider, etc) and additional data sources (laboratory data, etc). This is preferably done by computer programs that use Natural Language Processing algorithms to extract data from the diverse sources to determine an initial profile. However, the patient's initial profile may also be created, at least in part, by the healthcare provider manually.

Information contained within the profile is used to assign content in the form of 'dialogs 100'. In assigning content, the system takes into account the relative importance of treating that particular context of disease (P), the level of risk or the risk state (R) the particular patient is in, and a correction factor (F) that allows comparison of the R and P of different contexts.

Replies to the content are used to make changes to the profile, and further content is assigned on the basis of the updated profile. In this manner, a dynamic feedback loop is created whereby one day's results change the patient profile, and the updated patient profile is used to select the most appropriate content to fit the need.

This simplified view depicts the underlying basis of content assignment. However, in order to improve the effectiveness of the system, it would be necessary to take into account—

1. Reliability of the data provided by the patient. If the data provided by the patient is inherently unreliable, then health education, analyses, and medical advice provided on this basis would be fallacious.
2. Resistance of the patient to modify health related behavior. Resistance is inversely proportional to the level of motivation in the patient. A well motivated patient is more open to changing health related behaviors, with a view to improve his/her health status. However, motivation per se is not static, and it is possible to increase the patient's level of motivation (openness to change) by providing information that is in keeping with the patient's motivational drivers (emotive or driving force that is behind all human actions)
3. The patient's attention span. Patients have only a limited attention span, which further varies on a day-to-day basis, depending on the patient's other commitments: and a health management system that doesn't take this into account at content delivery is bound to suffer from poor compliance and continuation rates. Educational dialogs would need to be small enough to deliver the message within the patient's attention span, yet be capable of delivering more information on a specific aspect wherever requested by the patient.
4. The patient's personal preferences and type of remote terminal 72. In order that the system be most effective, it is preferable that the content presentation be customized to the patient's preferences and utilize the data display capabilities of the remote terminal to the fullest extent possible.

Method to Prioritize in Automated Content Assignment

Let
C be the context or attribute of the patient's health condition which is computed and followed by the system, and is the basis of which further automated content assignment. C in a patient with diabetes can include the blood glucose control attribute, medication compliance attribute, feet care attribute and long-term complications attribute.
N be the identification number of a patient.
R be the risk score that is computed in a particular context for a particular patient at time T
T is the time designator of a particular point in time.
M, the modifying factor is applied to R on the basis of replies received to queries
L be the reliability index of any given R value.
Further, let P be the priority sequence value of a context within any health condition.
F be the care provider defined correction factor for R values of any specified context. F values vary with the R scores of the specified context.
Z, the cumulative sequence is obtained by multiplying R, P and F. for a context.
W, the resistance factor indicates the degree to which a patient exhibits resistance to prescribed therapy.

Risk Scores (R Values)

R values signify the risk state or level of the patient. The R variable depicts the risk state or level of risk the individual within a particular context. It is also possible to create cumulative R values that are derived either arithmetically, or through the use of logical expressions, from different variables in the profile. Variables within the profile database, including the R value may be discrete or continuous variables.

Discrete variables include the individual's actual responses to queries, and are stored as such within the profile database, whereas continuous variables are arithmetically derived from the replies of the patient. In those instances where continuous variables are used in a context, the profile database additionally records the discrete variables, and the methods used to compute the continuous variable (numerical figure). Variables can also be a logical expression or a binary state.

When a patient is first registered into the system, he/she is assigned Risk values on the basis of data from medical records database 62, medical claims database 58 and additional material 54, by the use of Natural Language Processing Algorithms. Further, R values may be assigned manually by healthcare provider 60.

R values are subject to numerical manipulation on the basis of replies 134, measurements 74D, besides that from data contained within medical records database 62, medical claims database 58 and additional material 54.

R can be any positive decimal number greater than Zero. In case where R values have not been assigned from any of the abovementioned sources, R takes the default value of 1. A patient with greater R values for a given context has a higher risk of developing health related complications pertaining to that context. Conversely, a patient with a lower R value is better placed than a patient with a higher R value with regard to that particular context.

In the instance where R is a discrete variable, it instead takes on the value of a state, the R state. R states include text strings ('Feeling great', 'Not feeling so good', 'Terrible'), or a logical value ('Yes', 'No', 'Not sure').

R values are also serially followed in time (Time designator 'T'). Newer R values are usually mathematical functions of recent R values, and are directly linked to replies through the means of actions 140. For instance, healthcare provider 60 may create dialog 100 such that when individual 70 chooses one particular reply, the new R value equals the recent most R value multiplied by factor 'M', where M is any positive number.

ACTION 1: IF REPLY='YES' THEN NEW R=OLD R multiplied by 0.5
ACTION 2: IF REPLY='NO' THEN NEW R=OLD R multiplied by 2.0

In the instance where discrete variables are used, the actions may be so modified that, ACTION 1: IF REPLY='YES' THEN NEW R='Yes'
ACTION 2: IF REPLY='NO' THEN NEW R='No'

If assigned value 'M' for a particular reply is greater than one, then, the risk R increases, since any number multiplied by a positive number greater than one increases in value. On the contrary, if M lies between 0 and 1, the R value would decrease. So, provider 60 would assign M values to replies 134, in the form of actions 140 based on what a particular reply signifies in any individual's health condition and context. However, it would also be possible for healthcare provider 60 to 'reset' R to default, or any other value. The mathematical function applied here is:

ACTION 3: IF REPLY='NOT SURE' THEN NEW R=1.0
ACTION 3: IF REPLY='NOT SURE' THEN NEW R='Unknown'

Even as new R values are generated by the system as a result of replies 134 to queries and measurements 74D from monitoring device 74, older R values are archived within the profile database. Serially following R values of a patient is used in determining the progress made in the management of the patient's condition, in comparing the success of management protocols in the given patient, and in monitoring the progression of the chronic disease that is irrespective of management.

R values of different contexts for a given patient vary independently of each other. However, it would be possible for the provider to create summary R values that are a mathematical function of two or more R values.

$$R_{CUMULATIVE} = R_1 * R_2 * R_3 * R_4$$

In the instance where discrete variables are used,

IF REPLY1 = 'YES'; REPLY2 = 'NO'; REPLY3 $\geq$ 300,
THEN $R_{CUMULATIVE}$ = 'High risk'
ELSE IF REPLY1 = 'NO'; REPLY2 = 'YES'; REPLY3 $\geq$ 300,
THEN $R_{CUMULATIVE}$ = 'Moderate risk'
ELSE IF REPLY1 = 'NO'; REPLY2 = 'YES'; REPLY3 $\leq$ 300,
THEN $R_{CUMULATIVE}$ = 'Low risk'
ELSE $R_{CUMULATIVE}$ = 'Error: Incompatible data'

Reliability Index (L Values)

L, the reliability index of a given R value is indicative of level of confidence with which the R value depicts the actual risk faced by the patient within a context. L is proportional to the total quantum of data pertaining to a context that has been inputted, and subsequently used by the system in the computation of R values. L values for an R value assigned by default would equal zero, since no data was used in deriving the default value. It would also be possible for individuals 70 to be assigned negative L values indicating poor reliability of the veracity of the individual's responses.

L values are to ensure standardization and uniformity of R values, comparability of R values of different patients, and to correct a possible source of error within the system. Consider the following example; two diabetics, patient A and patient B with similar R values in the context of blood glucose control have been on follow up for 2 years, and 1 month respectively. Surely the confidence that may be placed by provider 60 on the R values of patient A is more than that of patient B, since considerably more data has been used in computing the R value of patient A. Patient A may have been a high risk patient who has subsequently modified his disease related behaviors, while patient B may have been assigned her R value by default. If one were to compare the results of a particular intervention, such as a new drug in the two patients without considering their L values, there would likely be fallacious results.

Further, R values are also used in decision making when replies are received. For instance, say patient A is assigned a low risk in the context of blood glucose control. If an isolated blood sugar measurement 74D is returned as high, then the test result may even be ignored along with the additional assignment of the task of repeating the test after a few days. On the contrary, if patient B were to return the same high blood glucose test result, considering that the validity (L value) of his/her R value is still uncertain (a default R value gives no information at all), the further follow up would likely be different. In this case, the assignment of an M value less than one would be appropriate.

It is obvious that as and when more data is entered into the system on a particular context, the L value for the particular derived R value would increase, since more computations would have been performed on the original R value to derive the current R value. It would be additionally possible for a provider to exclude R values from the automated decision making process when it's corresponding L value is below a defined value.

It is additionally possible to program L values to decrease when responses from individual 70 are inconsistent over time and incompatible with existing available data in the system. This is particularly relevant in the diagnosis and treatment of psychiatric conditions. In certain psychiatric conditions, such as Munchausen's syndrome, patients tend to live in a false world of their own creation. It becomes very difficult to diagnose the existence of this condition in the first place since the patients seem to be perfectly at ease with their own perception of events, which is however, grossly inconsistent with reality. Strategies employed by mental health professionals include repeating the same question to the patient after a span of time, repeating the query in another context and rephrasing the query and putting it to the patient. When gross inconsistencies are observed in any of the above, the suspicion of a disease process increases.

The same strategy is implemented in the system in the following manner: consider dialog D that queries the patient about a particular aspect of his/her life. Provider 60 simultaneously creates three more 'clone' dialogs, $D_1$, $D_2$ and $D_3$ which elicit the same information, albeit by putting the queries in a different manner, or as variants. Then provider 60 schedules dialogs $D_1$, $D_2$ and $D_3$ to appear on different days, and in different locations within a daily session (the beginning, the middle or the end) and interspersed between other queries. The interval between the patients' undergoing the two 'clone' dialog sessions may be days or even weeks.

Replies to $D_1$ are stored in the profile database. Additionally, actions may also be programmed to modify the value of R within a given context. Alternatively, the replies to $D_1$ may be directly compared with prior data within profile database for coherence, consistency and compatibility in view of R. When replies to $D_2$, and $D_3$ are received, they are directly compared with that of $D_1$. In case there is a significant variation in the replies to the three dialog 'clones' the L values will decrease, and, as a consequence it is determined that data received from the patient is not entirely reliable.

This would cause the healthcare provider to discount earlier data that the patient may have supplied, including that in a different context of disease. Further, it may be considered necessary at this stage to corroborate patient supplied information with that from the patient's friends, relatives, and significant others who know the patient since the unreliability of patient supplied information is established.

Content Assignment Mechanism—

Different contexts represent different aspects of the patient's condition. Likewise, these contexts occupy different priorities in the management of the disease process. Some contexts would need to be managed expediently, while others, though pertinent to the disease management process, could be managed at a later date.

Consider patient A in the diabetes example above. Patient A is also a smoker, and smoking cessation encouragement modules are particularly relevant in this patient, since diabetics who smoke have a very high risk of developing coronary arterial disease. Thus smoking cessation remains a high priority. However, if patient A were to additionally have trouble controlling his/her blood sugar levels (measurements repeatedly return in the higher range) then controlling the high levels of blood sugar takes precedence over smoking cessation. On the contrary, if measurements 74 of patient A's blood glucose were to widely fluctuate with some values in the lower value range (this occurs in a variant condition called brittle diabetes) then preventing low blood glucose (hypoglycemia) is of more priority than preventing occasional high blood glucose values. This is because, in the presence of hypoglycemia, the brain starves of energy, and this can permanently damage the cells of the brain. Thus it is obvious that even within a disease condition, there are some contexts occupy a higher priority in immediate management (and in the context of the system, in immediate content assignment, since the attention span of the patient is limited)

Within the system, the provider assigns higher priority sequence values (P values) to those contexts, which if test true for high risk behavior, signs or symptoms, require immediate management and intervention, while that which may be managed at a later date are assigned lower values. P value can be any positive number, and is assigned by provider after considering the P values that have been assigned to other contexts within the same and related health conditions. Similarly, educational modules that deal with contexts which are assigned higher P values are automatically assigned higher P values than that of other educational modules.

The consideration of the R and P values of all the contexts of a patient's condition is otherwise sufficient to manually assign content by priority. However, in order to automate the content selection process and make the risk values of different contexts comparable, it is necessary to include a correction factor, F that varies with the computed R for each of the contexts. F values are assigned by the provider for each range of R values of a context C. This information is stored in a lookup chart, such as Chart 1 below:—

CHART 1

R-F lookup chart

| CONTEXT, C | P value | FOR R = | F = | Explanation |
|---|---|---|---|---|
| Hypoglycemia prevention | 100 | <1 | 1 | >1.0 risk is assigned when there have been one or more such episodes (as determined from dialogs) |
| | | 1-1.99 | 30 | |
| | | >2 | 100 | |
| Glucose control | 90 | <1 | 1 | |
| | | 1-2.99 | 20 | |
| | | 3-6.99 | 35 | |
| | | 7-10.99 | 80 | |
| | | >11 | 200 | |
| Smoking cessation | 50 | <0.1 | 0 | <0.1 signifies that patient is not a smoker. F = 0 is to make sure that the patient never receives smoking cessation modules, as it is irrelevant. |
| | | 0.1-0.99 | 10 | |
| | | 1-4.99 | 25 | |
| | | 5-9.99 | 40 | |
| | | >10 | 90 | |
| Weight reduction, | 45 | <1 | 0.1 | <1 means the patient is maintaining optimum weight, and any advice would only be towards encouraging weight maintenance |
| | | 1-2.99 | 10 | |
| | | 3-9.99 | 30 | |
| | | >10 | 60 | |
| Exercising | 30 | <1 | 0.1 | |
| | | 1-5 | 4.0 | |
| | | >5 | 8.0 | |
| Foot care | 30 | <1 | 0.1 | |
| | | 1-5 | 4.0 | |
| | | >5 | 8.0 | |
| . . . more contexts | . . . | . . . | . . . . . . | |

The contexts depicted above are for the purpose of illustration only. By no means must it be considered comprehensive. In the actual diabetes treatment program, monitoring would be done on a far greater number of contexts than that depicted here, and in charts 2 and 3.

The hypoglycemia prevention context is assigned a very high P value=100, and when R>2, the F value equals 100. Similarly in glucose control, when R=8, F equals 80.

In prioritizing at the time of content assignment, content assignor 28 uses Z values which are numerically derived by multiplying R, P and F for each of the contexts. Dialogs corresponding to the context with the highest derived Z value are assigned to the patient at the start of each new session. However, in prioritizing content assignment for those contexts where R exists as a state (logical expression, text string or value), the above expression will not hold true. In this instance, the provider has the following options.

Firstly, the healthcare provider may arbitrarily assign R values for each of the possible R states. For example, the R state 'Feeling great', to the query 'How are u feeling today' to a patient with depression may be assigned a low R value, since it represents a better prognosis in a patient with depression; and 'Feeling terrible' may be assigned a high R value.

Second, the healthcare provider may write the follow up into the actions itself. In this case, if the patient replies 'Feeling terrible', he/she is asked further queries that attempt to elicit the cause of his/her low mood. Alternatively the healthcare provider may create an action whereby the provider is immediately alerted to the fact of such a reply, so that it may be followed up by a telephone call, a personal visit, or the scheduling of an appointment.

Third, the healthcare provider may so program the protocols database such that when the R state for a particular context in a patient returns certain value, text string or logical expression, the protocols database automatically adds a specified dialog to the tasklist database for that individual.

Fourth, the healthcare provider may use the reporting interface and manually assign dialogs to those individuals whose profile database returns true for a specified R state, or a combination of R states.

Chart 2 (Z-value chart) shows the derived risk factors, and computed Z values for the same patient A at point of time='1 Nov. 2001'

CHART 2

| Context, C | P value = | R value = (From profile data) | Corresponding F = (from Chart 1) | Z value = P * R * F |
|---|---|---|---|---|
| Hypoglycemia prevention | 100 | 2.8 | 100 | 28000 |
| Glucose control | 90 | 2.5 | 20 | 4500 |
| Smoking cessation context | 50 | 2.2 | 25 | 2750 |
| Weight reduction | 45 | 2.1 | 10 | 945 |
| Exercising | 30 | 4 | 4 | 480 |
| Foot care | 30 | 2.5 | 4 | 300 |

In patient A, the top priority (and the assigned content dialogs) would be towards preventing the possibility of a hypoglycemic episode (Z=28000). Next in priority would be to control the patient's blood glucose levels (Z=4500), and so on. At this point of time, automated content would primarily focus on the above two contexts, though 'maintenance' content would be assigned for the remaining contexts, namely smoking cessation, weight reduction and foot care. Further, regardless of the priority assigned to any context, when significant resistance is encountered (high W values), the automated content assignor provides only maintenance content for that context.

Over the next few weeks, the patient interacts with the system, and as a result, learns more about his/her condition, and is motivated to change sonic of his/her health related behaviors. It is also possible, especially in the case of diseases that run a more rapid course, that there has been progression of the condition in the meantime, which is independent of the medical management. As a result of the above the R values of the patient change in either direction for different contexts. At this point of time, the Z-value chart would read in the manner of chart 3 given below—

CHART 3

| Context, C | P value = | R value = (From profile data) | Corresponding F = (from Chart 1) | Z value = P * R * F |
|---|---|---|---|---|
| Hypoglycemia prevention | 100 | 0.9 | 1 | 90 |
| Glucose control | 90 | 1.6 | 20 | 2880 |
| Smoking cessation context | 50 | 1.5 | 25 | 1875 |
| Weight reduction | 45 | 1.5 | 10 | 675 |
| Exercising | 30 | 3 | 4 | 360 |
| Foot care | 30 | 2.1 | 4 | 252 |

Here, the highest priority is given for (and consequently, maximal dialogs assigned would relate to) glucose control Z=2880. Following this, priority would be assigned to smoking cessation and weight reduction respectively. The reduction in the R value of hypoglycemia prevention context is likely the result of patient education about the symptoms of hypoglycemia and the techniques that are used to prevent hypoglycemia when self administering insulin. Z values that are at this level (z=90) may be safely managed by 'maintenance dialogs', which reinforce in the patient, at regular intervals, the need to avoid hypoglycemia. Similarly, if significant resistance were encountered to smoking cessation context meanwhile, then the system would revert to 'maintenance dialogs' in that context. In the above example, the Z values for glucose control have also reduced from 4500 to 2880, but this still represents an area of high priority, and at this juncture, a significant portion of the content would still relate to this context of health care. The R value for foot care has decreased from 2.5 to 2.1, but with a Z score of 252, this remains one aspect of the disease that would require the provider's attention.

For reasons of clarity, the above example illustrates the change in assigned content after the passage of a span of a few weeks. However, it must be understood that in the actual system, dynamic updating of the profile and content assignment would take place in real time, such that the system responds in real time to the changing profile of the individual patient. Maintenance dialogs are communicated with patients who are otherwise at low risk states for a particular context, in order to ensure the patient's sustained interest in the disease management process, as also to reinforce in the patient knowledge and correct attitudes regarding the disease context.

Measurements 74D from monitoring device 74 may be used, in addition to modify the computed R values by assigning 'M' values to ranges of values of 74D. In the case of diabetes, monitoring device 74 may be a glucometer, and dialog 100 may be so programmed that when blood glucose levels are above a certain value, the old R value ($R_{GLC-OLD}$) gets multiplied by a certain factor $M_1$ to yield a new R value ($R_{GLC-NEW}$). In the logical expression given below, $M_1$ is the returned post dinner blood sugar value from monitoring device 74 of patient A, in milligrams per deciliter (measurement 74D).

ACTIONS:

```
IF M₁ >500,
    THEN R_GLC-NEW = R_GLC-OLD * 3.5 ;
    THEN FOLLOW PREACUTE DIALOG 1001.
ELSE IF 300 ≤ M₁ ≤ 500,
    THEN R_GLC-NEW = R_GLC-OLD * 1.8;
    THEN FOLLOW EDUCATIONAL DIALOG 16.
ELSE IF 200 ≤ M₁ ≤ 300,
    THEN R_GLC-NEW = R_GLC-OLD * 0.8;
    THEN FOLLOW CONGRATULATORY DIALOG 22.
ELSE IF M₁ < 200,
    THEN FOLLOW LOW PD-GLUCOSE DIALOG 11.
    IF LOW PD-GLUCOSE DIALOG 11 = POSITIVE,
        THEN R_HYPOGLY-NEW = R_HYPOGLY-OLD * 1.6
```

If the measured blood glucose values exceed 500 mg/dl, then the risk factor increases by a factor of 3.5 and PREACUTE DIALOG 1001 is followed. If the measured blood glucose were to be between 300 and 500 mg/dl, then the risk factor would increase by 1.8 and an educational dialog would follow. However, if the returned values were in the normal range (200-300 mg/dl) a congratulatory statement would follow. If the values were on the lower range, a hypoglycemia prevention statement would follow. In this manner, it is possible to detect a developing complication and intervene early, in order to prevent the condition from worsening and presenting at a stage where it is more difficult and expensive to manage.

In addition, R values can be modified on the basis of the results of laboratory tests, data contained in medical records database 62, medical claims database 58 and additional material database 54. In the diabetes example, a lipid profile test done at the laboratory of the healthcare facility or elsewhere (additional material database). Similarly the failure of the patient to keep up an appointment at healthcare provider 60 can also be used to increase the R value for a context.

Resistance Factor (W)

W, the resistance factor is particularly relevant in the management of chronic illnesses, where there is a tendency for patients to become non-compliant with medical regimens with the progression of time. While individualization and customization of the dialogs and management plans helps to prevent this to a great degree, it is also necessary to identify and quantify developing resistance at an early stage, and suitably modify the mode of management. W, the resistance factor quantifies the degree to which the patient is non-compliant with the treatment plan, whatever be the reason, in order that alternative approaches are explored.

Resistance in a particular context is inversely proportional to the motivation of the patient with regard to the particular context. Further, this motivation is amenable to change, as a result of information provided to the patient on the importance of that context in the entire health management process. So, when a patient is exhibiting high resistance in a context, the dialogs assigned to the patient take on the 'maintenance mode'. 'Maintenance dialogs' differ from the 'conventional dialogs' in that these dialogs are 1. presented to the patient at a frequency that is less than other contexts with similar Z values,
2. intended to stimulate the patient's interest and curiosity, rather than stimulate the patient to change his/her health related behavior,
3. intended to convey information in a non-opinionated manner, and allow the patient to draw his/her own conclusions, and
4. at least one reply to each query or teaching statement allows the patient to terminate the dialog relating to that context.

Chart 4 is similar to Chart 3, with the addition of a column depicting the resistance (W) values for each of the contexts.

CHART 4

| Context, C | P value = | R value = From profile data | Corresponding F values (from Chart 1) | Z value = P * R * F | W value |
|---|---|---|---|---|---|
| Hypoglycemia prevention | 100 | 0.9 | 1 | 90 | 2.6 |
| Glucose control | 90 | 1.6 | 20 | 2880 | 2.5 |
| Smoking cessation context | 50 | 1.5 | 25 | 1875 | 25.1 |
| Weight reduction | 45 | 1.5 | 10 | 675 | 0.5 |
| Exercising | 30 | 3 | 4 | 360 | 0.5 |
| Foot care | 30 | 2.1 | 4 | 252 | 1.0 |

The W values for smoking cessation are quite high (25.1) in this patient. So the patient is put on maintenance dialogs for this context till the issue is resolved by a patient-provider personal interaction, or the W values show a decreasing trend as a result of the maintenance dialogs. A pro-active stance of attempting to achieve total smoking cessation is deferred until then, for the abovementioned reasons. If it is determined, as a result of the patient-provider interaction(s), that the patient will actively work towards achieving complete cessation, the W values and/or R and L values may be 'reset' to default levels by the provider, by accessing profile database directly, or by the use of a custom action at dialogs 100.

As is evident from Chart 4, resistance values are independent of R, P, and F values. This is because the method for the derivation of W values is different from the method of derivation of the remaining values. R depicts the risk status of the individual within a context, while W has more to do with the level to which the patient is motivated (or resistant) to the context under question.

Consider another example: Patient H is on follow-up for coronary arterial disease (clogging of the blood vessels, the cause of heart attacks). Patient H is also a chronic smoker, and it is well known fact that quitting smoking remains the single best intervention in this patient that will reduce the patient's risk of developing heart attacks and strokes in the future. So the content assignor 28 would commence intensive efforts to achieve smoking cessation in this individual, by the use of education modules. Hopefully, this will cause the individual to quit smoking. However, a subset of patients may be put-off by these messages, and consider them intrusive to their lifestyle, which may lead to an increased dropout rates and non-compliance with the remainder of medical management provided by the system. In these patients, smoking cessation still remains a long-term goal but it is recognized that conventional dialogs may prove to be counter-productive. Instead, maintenance dialogs such as the one depicted below, are communicated to the patient.

[MAINTENANCE DIALOG IN A RESISTANT SMOKER]

1. A RECENTLY CONCLUDED STUDY CONFIRMS THE FACT THAT SMOKERS ARE TWICE AS MORE LIKELY TO DEVELOP IMPOTENCE DUE TO VASCULAR CAUSES THAN NON-SMOKERS.
  A. OK [ACTION: GO TO NEXT DIALOG]
  B. MORE [ACTION: $W_{SMOKER-NEW} = W_{SMOKER-OLD} * 0.8$;]
      [ACTION: GO TO DIALOG 'SMOKER-IMPOTENCE-101']
  C. SKIP [ACTION: $W_{SMOKER-NEW} = W_{SMOKER-OLD} * 1.5$]
      [ACTION: GO TO NEXT DIALOG]

The patient is informed about the harmful effects of smoking, more as a teaching statement or a news headline, than as an attempt to induce him/her to quit smoking. The idea here is to provide information, and stimulate the patient's interest, and to arouse the patient's curiosity. Responses to statement include 'Ok', 'More' and 'Skip'. If the patient chooses 'Ok', the next dialog within the program is served to the patient. If the patient chooses 'More', it means that the patient is curious about this aspect. So, in addition to providing the patient more details of the study, the value of resistance in the context of smoking cessation is reduced by a multiplying it with 0.8. On the contrary, if the patient decides to 'Skip' the statement, the value of resistance is increased.

When resistance increases above a certain operator-determined value, it is obvious that the problem is unlikely to be solved by remote dialogs alone, and alternative approaches are explored, including bringing up the topic at a personal interaction, such as an interview, or a telephone conversation.

After any dialog is presented to the patient, a marker is placed in the profile of the patient regarding the same, in order that the content assignor does not automatically present the same dialog to the patient more than once. However, the same dialog may be presented to the patient at the discretion of the provider.

Methods to Avoid the Development of Resistance—

Dynamic dialog paradigm—In this paradigm, possible replies to query include 'Skip Query'. When this option is chosen by the patient, the program at remote terminal 72 proceeds to the next query, and a marker indicating the particular reply is added to profile database 44. Additionally, a task may also be added to the tasklist database 46. This task can include serving the dialogs to the patient at a later date and in an alternative format.

When implemented, dynamic dialog paradigm allows the patient to dodge a query. This is because; some queries can be very personal or embarrassing to patients. Further, not all patients are forthcoming when initially queried regarding such topics as domestic abuse, usage of psychotropic substances, etc. In diseases such as mood disorders, it is not uncommon for patients to abuse psychotropic substances in a misguided attempt to 'treat' their condition. Though the topic may be better discussed with the patient at a personal interview, it is advantageous to screen patients using the remote monitoring system, to identify those patients in whom this aspect needs to be further elucidated.

By allowing the patient to 'dodge' a query, the healthcare provider identifies those individuals who have reasons not to reply to the query. In the instance that a patient 'Skips' a query, this aspect is either explored at a future personal visit, or by a dedicated dialog for eliciting responses from this subset of patients.

If this option were not available to the individual, it is likely that a considerable proportion of patients would simply deny the condition, thus making the data unreliable. Thus, dynamic dialog paradigm has the net effect of increasing the reliability and veracity of the data entered into the system and available to the healthcare provider.

Online dialog dynamism—In order to sustain the patient's interest and continued attention in health management and educational materials, it is necessary that the content adapts itself to the attention span and interest of the patient. It is further necessary that patients progress through the program at their own pace, and that the content matches evolving patient status or the evolving understanding of the patient condition. Since the patient's perception of the health benefits to be derived from the system tend to vary with time, it is important that the focus of interaction be dictated by the user wherever possible and that the dialog is responsive to the individual in real time (Online dialog dynamism) For example, on a particular day, individual 70 might not be keen on completing his/her educational module, while on another day, a topic in the module might stimulate the individual's interest, and he/she may wish to learn more about it.

Online dialog dynamism allows patient's replies to change the presented content in real time without the invoking of communication system 50. Replies to a teaching statement can include 'Ok, 'More' and 'Skip'. If the user selects 'Ok', the teaching statement proceeds along the originally intended course. However, if 'More' is chosen by the patient, additional latent teaching statements from content 130 are invoked. On the contrary, if 'Skip' is chosen, the teaching statements are terminated, and are invoked at a later date. 'Skip' invoked within online dialog dynamism will not normally modify the resistance factors, though it is possible to program it to do so.

Customization—At the time of registration of the patient into the system, the patient is queried regarding the preferred remote terminal 72 and monitoring device 74 with which the patient is to communicate with the system. Other preferences include whether the patient prefers audio, videos and other multimedia components (including video games) as a part of the content (wherever supported by the remote terminal and communication network 50). Another point where customization may be implemented is in the frequency, timing and total amount of dialogs served to the patient, as a part of the interaction.

Additionally, customization may be in relation to the scheme and mode of presentation of content on the display screen of remote terminal 72. In the preferred embodiment, the customization components are stored in profile database 44 in the profile computer 20. In an alternative embodiment, these components are stored in remote terminal 72 and/or monitoring device 74, and script programs received from profile computer 20 are automatically customized at the level of the terminal 72, and device 74, and then presented to the patient.

Customization is aimed at making the system more user-friendly and capable of optimally utilizing the data transfer capabilities of communication network 50, and the display and processing capabilities of remote terminal 72 and monitoring device 74. In one embodiment, the patient provides the details of his/her devices and communication network. For example patient may be asked to choose among a list of supported devices and type of content. In an alternative embodiment, the profile computer 20 detects the type of remote terminal 72, monitoring device 74 and communication network 50, and optimizes the content for delivery. For example patients who are connected by a low-speed 36 kbps modem would have lesser amount of multimedia content served to them than those patients in whom communication is established by high speed internet. Specific techniques of implementing this are well known in the art.

A few examples of specific instances where customization of the dialogs to the remote terminal 72, monitoring device 74 and communication network 50 is particularly advantageous are given below.

PDA (Personal Digital Assistants)—

| | |
|---|---|
| Integration of script programs with the daily task planner program within the PDA. | Patients may be reminded to take medications on time, in the form of alerts. Appointments with the healthcare provider may be automatically scheduled on the basis of entries in the planner. |
| Serial recording of parameters measured by device 74. | Graphical representations of the parameters, e.g. blood glucose levels may be created at the level of the terminal 72 itself, with regular updating of the profile computer. The patient may communicate with the system less often, with the one-time transmission of stored data in the intervening period. |
| Symptom diary maintenance | A patient with depression, epilepsy, asthma, etc may create entries, and even store measurements 74D in a symptom diary program that stores the data within the terminal 72. At regular intervals, or when the local processing algorithm determines that the patient is at increased risk, he/she is advised to contact the healthcare provider immediately. In the case of asthma, the additional advantage is that the daily activities of the patient may be correlated with the PEFR (Peak Expiratory Flow Rate) values of the patient, which is an objective measure of the severity of disease, in order to find what factors actually are responsible for the exacerbation of the patient's condition. Additionally, subjective-objective studies may be performed whereby, for example, the PEFR is compared with the patient's subjectively reported symptoms. |
| Enhanced rich multimedia content suited to the patient's disease state. | There are no limits as to the bandwidth of transmitted content within Digital TV, and rich multimedia and audio containing data streams may be transmitted. Patients who need to exercise are shown provided daily videos of weight reducing exercises to help them in their workouts. This may be scheduled at the patient's convenience. Patients may be shown videos of former smokers recounting their personal experiences with smoking cessation, as a psychological support mechanism to encourage them to try and quit smoking. Support may extend into the critical quitting phase, especially where the patient is experiencing withdrawal symptoms. |

PC (and also PDAs) Connected to High-Speed Internet—

| | |
|---|---|
| Speech generation and voice recognition programs | Instead of receiving written queries, a computer generated face reads out the queries. Replies are received by deciphering the voice of the patient, so that no text input is required by the patient. The same applies also to the maintaining an electronic symptom diary. |

Monitoring Device 74 Directly Connected to Communication Network 50—

| | |
|---|---|
| Automatic measurements of physiological parameters with direct communication to profile computer 20. | Bathroom scales (device 74) of patients with congestive heart failure are connected through terminal 72 or directly to profile computer 20. An increasing weight over a few days or weeks is used to activate a script program in the terminal 72, either directly or after going through profile computer 20. A similar method is adopted in the case of diabetes, whereby an unusually high blood sugar level is used to activate a script program in terminal 72. In the case of asthmatics, a low PEFR is used to activate the script program in terminal 72. |

Though specific instances are displayed for specific remote terminals 72, with the increasing convergence of technology, it may be possible in the near future for some remote terminals to perform the functions that have been described with other remote terminal 72. Further, the specific instances listed above are for illustrative purposes only, and are not meant to limit the scope of the invention. Many other variations of the above may be generated and transmitted to patients in alternative embodiments.

Serial Follow up of R, L and W Values, and its Implications in Patient Management:

Since the R values are measured in arbitrary units, serial follow up of the values in a patient provides far more information than that provided by a single value. Different combinations of the trend in R, L and W values with respect to time identifier 'T' suggest a variety of possibilities, and this may be used in patient management. This is illustrated by factor combinations 1 through 5 below:

Factor Combinations the actual management process. In some cases, however, the confirmation step may be skipped and one may directly go to the step of intervening urgently. Approaches for urgent intervention in the patient may include a personal visit to the patient's home, fixing up an appointment at the healthcare facility, a telephone call to the patient and/or his/her loved ones, and the usage of dialogs that enable the more intensive monitoring of the patient, at least until the patient is considered out of risk. The advantage of earlier detection and intervention in the patient's condition is that interventions done at this time are more efficacious, less expensive, and demand fewer resources on the healthcare system—in terms of time and personnel.

| RISK FACTORS, R | RELIABILITY, L | RESISTANCE, W | IMPLICATION | MANAGEMENT STRATEGY |
|---|---|---|---|---|
| 1. Isolated high risk result or rapidly deteriorating risk factors in one or more contexts. | More or less constant | More or less constant | Patient's health status is worsening. Patient may be 'pre-acute'. | Follow-up dialog to determine the cause of this sudden deterioration in health status. To rule out fallacious results. Alert provider to the case, who may establish contact with the patient by phone or personally. |
| 2. Slow deterioration in R factors in a previously well patient. | More or less constant | More or less constant | Probably disease progression that is irrespective of the management. | Confirm whether disease is really progressing, by the use of diagnostic tests and measuring disease related parameters, and at personal visits to healthcare facility. Manage accordingly. |
| 3. Patient is gradually deteriorating with regard to R factors (R value is increasing). | More or less constant | Increasing | Patient probably feels that the system is not helping him/her much since he/she is doing quite well on the health related parameters anyhow. There is a high likelihood of losing this patient to follow-up. | Reduce the content on those contexts where the patient is showing resistance. Likewise, increase the content on those contexts where the patient has requested more information at any time. Provide 'maintenance content', that teaches the patient the importance of continued follow up and compliance, even if otherwise asymptomatic, or feeling well. |
| 4. Any value | Decreasing or low reliability in a single context | High for that context. | Information about this context is not reliable when obtained remotely by the system. | This aspect would need to be explored at a personal interview, and after the patient's confidence has been secured. This context may, in fact hold the key to the diagnosis, and the patient's condition may never be cured completely without resolving this. |
| 5. Any value | Decreasing or low reliability spread over multiple contexts. | Any value. | Information obtained from the patient is inherently unreliable. | Obtain information from other sources such as the patient's friends, relatives, and employers/co-workers. Consider the possibility of malingering. In psychiatric patients, rule out underlying psychosis. |

Factors Combination 1

Progressively deteriorating (increasing) R values over multiple contexts in a patient over a short period of time, with more or less constant reliability and resistance suggests that the patient's health status is deteriorating. The patient may be in the process of developing an urgent 'pre-acute' condition, which, if left untreated may rapidly progress into full blown disease. The first step would be to confirm the fact of the existence of the pre-acute condition, and this is followed by Earlier detection of 'pre-acute' conditions for the purpose of intervention is implemented by the use of standardized questionnaires and dialogs that look for the presence of 'sentinel signs and symptoms' that represent the earliest warning signs of deteriorating patient's health. In the case of diabetes, include an isolated abnormally high blood glucose measurement (diabetic hyperosmolar coma) or an episode of sweating accompanied by palpitations and drowsiness (hypoglycemic attack).

Logical expression below depicts the PREACUTE DIALOG 1001 that is assigned when there is an isolated blood sugar test result of greater than 500 mg/dl (precursor of diabetic hyperosmolar coma)

---

PREACUTE DIALOG 1001 [$M_1 > 500$]
QUERIES:
1. DID YOU FORGET TO TAKE ONE OR MORE DOSES OF YOUR MEDICATION?
   A. YES [ACTION: SERVE DIALOG 'COMPLIANCE 21']
   B. NO [ACTION: GO TO NEXT QUERY]
2. DID YOU HAVE AN UNUSUALLY LARGE MEAL?
   A. YES [ACTION: SERVE DIALOG 'COMPLIANCE 23']
   B. NO [ACTION: GO TO NEXT QUERY]
3. DO YOU HAVE ANY OF THE BELOW: FEVER/FEELING UNWELL/NAUSEA?
   A. FEVER [ACTION: SERVE DIALOG 'ACTIVE INFECTION 91']
   B. FEELING UNWELL [ACTION: SERVE DIALOG 'MALAISE 92']
   C. NAUSEA [ACTION: SERVE DIALOG 'ACTIVE INFECTION 92']
   D. NONE OF THE ABOVE [ACTION: GO TO NEXT QUERY]
4. PLEASE REPEAT A BLOOD GLUCOSE SAMPLE {REPEAT M1}
   A. REPEAT $M_1 \geq 500$ [ACTION: GO TO NEXT QUERY]
   B. REPEAT $M_1 < 500$ [ACTION: ADD INFO TO 'ERROR.LOG']
5. YOUR BLOOD SUGAR LEVELS ARE DANGEROUSLY HIGH!!! IF LEFT UNCHECKED YOU MAY DEVELOP SERIOUS COMPLICATIONS. PLEASE SELF ADMINISTER 8 UNITS OF INSULIN AND CHECK YOUR BLOOD SUGAR LEVELS 8 HOURLY.
   A. OK [ACTION: FOLLOW DIALOGS 'INTENSE MONITOR 67';]
      [ACTION: ADD TASK 'CHECK BLOOD SUGAR 11' 8 HRLY]
      [ACTION: ALERT PROVIDER IMMEDIATELY]

---

Since this high a blood glucose value places the patient at a particularly high risk for developing complications and has important implications for further management, it is necessary to know the exact circumstances under which the patient's blood glucose has reached these levels. This is done by asking the patient to reply to PREACUTE DIALOG 1001. Pre-acute dialog 1001 contains queries that attempt to rule out less worrisome causes of the high glucose levels. For instance, if the patient has forgotten to take his/her regular dose, then he/she is advised to take it immediately, and obtain a repeat blood glucose value after 2-3 hours. Likewise, if the patient has had an unusually large meal that particular evening, he/she is advised to add a little extra insulin to the usual nightly dose. Alternatively, if the patient reports that he/she has been running a fever or has been feeling unwell for a few days, an urgent visit to the healthcare facility is necessitated, since this level of blood glucose may be the earliest sign of developing diabetic hyperosmolar coma, a potentially serious condition where, in the presence of active infection, the blood glucose control mechanisms are seriously compromised, and which may rapidly progress to uncontrollable systemic infection, coma and death.

Further, if a repeat blood glucose test returns as normal, and it is determined that the high initial levels were a result of a technical fault in measuring device 74 (ERROR), then the information is stored in the ERROR.LOG file, and no further action needs to be taken, other than recalibrating or replacing monitoring device 74.

In the management of depression, a sentinel sign can include the patient's daily rating of his/her mood on a scale from one ('feeling low', depressed) to ten ('feeling great', happy). Other sentinel symptoms include the patient's sleep patterns, appetite, feeling of tiredness and activity, etc. The progressively worsening of the patient's risk factors on these contexts over a short span of time, such as a few days is picked up by the monitoring application, which in turn, may send dialogs to explore the reasons for the patient's worsening mood, or fix an appointment with the patient, or alert the healthcare provider depending on the preset protocol as determined by the provider. The provider may additionally initiate a phone call to the patient, or make a personal visit to the patient, or assign additional exploratory dialogs with the patient (Was there some recent setback at the workplace/at home, to dear ones/in relationships? Is the patient regularly taking his/her medications? Have suicidal thoughts ever intruded (suicidal ideation) into the patient's consciousness? etc)

For obvious reasons the patient may be advised to report to the facility immediately if he/she reports suicidal ideation. In addition to receiving alerts regarding the worsening mood status of the patient, the patients' non-response to dialog programs would constitute sufficient reason to alert the provider. This is especially more so when accompanied by a recent decreasing mood level in the patient (increasing R values).

Similarly, in the case of patients with congestive heart failure, a history of increasing swelling of the feet (pedal edema), decreasing urine output and episodes of breathlessness on lying down (orthopnea) would constitute 'sentinel signs' and be monitored for the purpose of diagnosing 'pre-acute' conditions. In this case an electronic weight scale serves as monitoring device 74.

Factors Combination 2

It is a well known fact in medicine that, while the treatment of chronic diseases improves the quality of life and increases longevity, the underlying pathological process remains unaltered, and often worsens with time. This necessitates an increase in the dosage of administered drugs, or the consideration of alternative modes of therapy. Further, the therapeutic effects of drugs and management tend to decrease on long term usage. For instance, diabetes patients develop the phenomenon of insulin resistance, whereby the body requires an increased dosage of insulin to control the blood sugar level to the same extent as earlier. Patients on oral hypoglycemic agents may require a switchover to injected insulin. Similarly, patients with HIV infection on anti-retroviral therapy would exhibit lowering CD4 counts, as a result of developing resistance of the virus to drugs.

Common to the above processes is the fact that the increasing risk factors takes place over a span of months, or even years. In these patients, there is a gradual deterioration of risk status (increasing value of R), especially the values that are derived as a result of objectively measured physiological parameters, and scored questionnaires. So, when this is seen in a previously well patient with more or less unchanged or improving L and W status, this indicates primary progression of disease. To confirm the above, the healthcare provider may additionally prescribe diagnostic laboratory tests, such as tests for anti-insulin antibodies in the case of diabetes, and Viral Load tests in the instance of HIV infection.

Factors Combination 3

Notwithstanding the mechanisms to increase the patient's compliance with medical regimens such as dynamic dialog paradigm, online dialog dynamism and customization, in a small subset of patients, resistance (W) to the system may show a gradual increase with time. This may be accompanied by a simultaneous increase in risk factors (deteriorating patient's health status). In patients with low pre-existing risk factors (well-motivated patients), this may be because the patient feels that he/she has not much to gain from the system, since his/her health status and management is low risk anyhow. On the contrary, some patients may be intrinsically less motivated, or less inclined to look after their health and may show high risk factors with high resistance.

Regardless of their present health status, both patient-groups are still at risk of deteriorating. Patients who exhibit this phenomenon will show gradually increasing resistance (W) values over multiple contexts, with or without accompanying deteriorating R values. Reliability values may also be adversely impacted. Continuing to remotely manage these patients without taking into account the developing resistance will have a negative impact on the effectiveness of treatment regimens and continuation rates for these patients.

Managing these patients would require that the patient is kept on 'maintenance content', content that is primarily educational in nature, and emphasizes upon the importance of continued follow up and compliance with medical advice, even if the patient is otherwise asymptomatic. Further, the patient is taught that many diseases remain under the surface and progressively hurt the body, and emerge after a 'latent period' even if they do not cause symptoms meanwhile. Further, there are as few as necessary dialogs initiated which pertain to the contexts where resistance is encountered.

However, some of these issues are likely to be better resolved at personal interviews and the monitoring application is crucial in that it serves to detect early and alert the provider to this happening, in order that a personal interaction is initiated.

Factors Combination 4

Every effort is made to query patients on sensitive topics in a non-opinionated fashion and in an open ended manner (by allowing the patient to elaborate). However some patients may still feel uncomfortable about answering queries that relate to sensitive topics. Some of these queries are relevant to the health condition, and can have a significant impact on the management, e.g. a history of psychotropic drug abuse in a psychiatric patient, a history of alcoholism in a depressed patient. Often these queries hold the key to the diagnosis and the patient's condition may never be treated wholly without resolving the particular issue. In addition, some queries, while not directly related to the patient's condition, if returned positive, can have a significant impact on management, e.g. a 70 year old lady on follow up for congestive heart failure is queried about possible elder abuse. The query however is needed to rule out one of the commonest causes of poor health in these patients, and is in the best interests of the patient.

As has been described earlier, patients are allowed the option of skipping the query, so that the provider is alerted to the fact that the patient has reasons whatsoever to 'dodge' the query. The reasons can range from the queries' being embarrassing to the patient (e.g. the screening for elder abuse query) to the patient's being uncomfortable with that particular aspect of his/her own life (e.g. alcoholism and drug abuse in a depressed patient) may simply wish to skip it.

High resistance implies that the patient has reasons not to answer the query, whatever the reason. When there is high resistance in a single or a few isolated contexts, with or without low reliability for these contexts, the information regarding this context within profile database would need to be elaborated by the provider. This aspect could be explored at a personal interview and after the patient's confidence has been secured. Alternatively this is done through the usage of dialogs that are more sensitive in their language, and of dialogs which look for indirect pointers towards the condition of interest. Alternatively, 'pointer queries' are used which query the patient on topics that are commonly associated with the health condition of interest.

For example, consider patient D on follow up for depression who gives a history of occasional alcohol intake. However, he says that he has no more than a couple of drinks a week, and denies that he has ever consumed alcohol as a result of his feeling 'low'. Ruling out alcoholism (different from 'social drinking' and moderate alcohol consumption) is very important in this patient, since his depression may in fact be a result of chronic intake of alcohol. It is a well known fact that alcoholics tend to downplay the actual level of their intake, so the patient's denying a history of alcoholism would not be of much value in the decision making process.

Instead the system attempts to assign risk scores for alcoholism by looking for indirect markers within medical claims database 58, medical records database 62 and additional material 54. These include a history of frequently presenting in the emergency room with cuts and wounds (acquired as a result of the drunken state), frequent lung infections (from aspiration of stomach contents), a history of being in a de-addiction program, the physician notes of prior consultations, results of old/recent laboratory tests that are associated with a high alcohol intake (a fatty liver, and cirrhotic changes seen on a CT scan done for some other reason, a raised blood Gamma-glutamyl-transferase enzyme levels), etc.

Further, the patient may be administered adaptations of standardized screening tests for alcoholism, such as the CAGE Test, either at a same sitting, or spread out over many sittings. If the screening tests and/or any of the indirect markers test as suspicious for alcoholism, this aspect is explored further through the use of dedicated dialogs or at personal communications with the patient.

In addition, patients who are former alcoholics, and who are on follow up for some other condition may be monitored for a recurrence of uncontrolled drinking in the same manner as detailed above. In this case, these patients may be monitored and provided supportive management in order to prevent the alcohol recurrence status.

Factors Combination 5

When the information obtained from the patient over multiple contexts has a low reliability, or the reliability factors are decreasing, this indicates that the information obtained from the patient is inherently unreliable. Healthcare management in these patients cannot be done on the basis of patient provided inputs alone, since the patient provided data is seen to be unreliable (inconsistent with known data) and possibly fallacious.

Malingering is the condition where a healthy person simulates symptoms of disease for personal gain. Malingerers often present to medical providers as difficult to diagnose, atypical cases. While this gives the provider an initial clue to the real cause of the patient's symptoms, it is seldom possible to make a sure diagnosis of malingering on this basis, in an individual patient. Further, some malingerers do not simulate new symptoms but simply exaggerate the severity of the disease state for the sake of gain, which may be financial compensation from a former employer, or an insurer; not having to go to work and sympathy from dear ones. Malingering is responsible for a significant portion of wasteful healthcare expenditure, and detecting this is a priority in any healthcare system.

An important characteristic of malingering is a frequent change in the patient's 'story' and inconsistency between the history and the severity of symptoms. It is often difficult for the provider to keep track of every single detail of the patient-provider interaction in order to seek inconsistencies in the history. Even if this were to be done, an attempt to visualize the data in the context of malingering would not prove to be worthwhile in view of the time, effort and cost expended.

This however may be done through the use of the system in the following manner: when the reliability is low for one or more contexts and there is an inconsistency in the risk factor scores obtained from different sources, the suspicion of malingering is raised. This is because malingerers do not report groups of symptoms in the manner that they usually present to a provider. This is different from Factors Combination 4 in that the unreliability is spread over multiple contexts, and that these contexts do not necessarily deal with 'sensitive topics', or those topics where an ordinary person would be uncomfortable in relatina to a provider.

Further, these patients are likely to exhibit high resistance, and this is spread over multiple contexts. This is because these patients have a constant underlying fear of being 'caught' and so try to avoid supplying additional data as much as possible. So, they are far more likely to choose 'Skip', when compared with a patient who is genuinely suffering from the condition.

The mechanism may be further refined such that within a dialog, there are no more than one or two queries of interest, which are interspersed within general queries pertaining to 'neutral' topics, i.e. those topics which are likely to put the individual off-guard with regard to the true significance of the query.

Factors Combination (Miscellaneous)

If a new intervention is planned for a specific condition, and is in relation to a particular context, such as a novel drug for the control of blood glucose, it would be possible to choose those patients who are having greatest difficulty in controlling their blood sugar levels based on their computed R values. This group of patients would likely represent the diverse background of patients with diabetes, with regard to other parameters. If a randomized study comparing the efficacy of the two treatments is planned, then the control group (patients who are not treated at all, or those who are placed on standard treatment) can consist of patients with comparable R values. The R values of patients following the new treatment can be followed to see the response of the glycemic control to the new drug. In this manner, R values may be applied in the context of conducting research studies, and clinical trials in the evaluation of new drugs, etc.

Improving R values that relate to the symptoms and quality of life factors, after the institution of a new drug would suggest that the new drug is more effective in controlling this given set of symptoms in the patient, and is more likely to be accepted in this patient.

A final advantage of the system is that there is huge research benefit in identifying parameters that can correlate to subgroups of patients who respond differently to treatment. All data relevant to the patient's health condition, including the patient's replies to specific queries are stored in the profile database, each in a separate column. Additional columns describe the response of the patient to specific medical interventions (in the form of the change in the R values as a function of time, i.e. pre-treatment and post-treatment values of R)

Chart 5 depicts an example profile database for a group of 10 patients on treatment for depression, who additionally consume alcohol. Some of the patients being followed up agree to cease consuming alcohol consumption completely, and are given support and motivation to do so, while the remainder patients are placed on the regular follow up schedule for depression. For the sake of clarity, only three contexts (1, 2 and 3) are shown in the chart. Cumulative L and W values for the patient are shown. However, in the actual study, the R, L and W values of more contexts, and more patients would be taken into account.

CHART 5

| | | R, P, F VALUES OF SPECIFIED CONTEXT | | | | | | | | |
|---|---|---|---|---|---|---|---|---|---|---|
| $R_i$ | CEASE | APRIL 2002 | | | | | JANUARY 2003 | | | |
| PATIENT | ALCOHOL | $R_1$ | $R_2$ | $R_3$ | $L_{ALL}$ | $W_{ALL}$ | $R_1$ | $R_2$ | $R_3$ | $L_{ALL}$ | $W_{ALL}$ |
| #1 | YES | 3.5 | 1.6 | 2.5 | 6.1 | 0.7 | 1.6 | 1.2 | 2.4 | 10.1 | 10.4 |
| #2 | NO | 1.6 | 5.1 | 1.9 | 2.8 | 0.9 | 1.5 | 5.5 | 1.7 | 2.5 | 0.9 |
| #3 | YES | 11.5 | 5.3 | 4.1 | 9.1 | 1.4 | 6.1 | 2.1 | 2.8 | 10.1 | 1.2 |
| #4 | NO | 1.2 | 1.4 | 1.7 | 12.1 | 0.4 | 1.1 | 1.2 | 1.5 | 12.2 | 0.4 |
| #5 | NO | 10.6 | 6.2 | 3.8 | 14.1 | 1.7 | 8.1 | 4.2 | 3.4 | 11.2 | 1.8 |
| #6 | NO | 5.5 | 4.0 | 2.2 | 8.1 | 5.4 | 3.9 | 6.1 | 2.6 | 8.2 | 4.3 |
| #7 | NO | 3.4 | 1.3 | 2.8 | 7.5 | 0.9 | 2.8 | 1.2 | 2.6 | 7.4 | 0.7 |
| #8 | YES | 1.0 | 1.2 | 1.1 | 9.8 | 0.6 | 1.0 | 1.3 | 1.2 | 9.6 | 0.5 |
| #9 | YES | 5.4 | 4.1 | 2.1 | 0.4 | 1.7 | 3.7 | 6.4 | 2.3 | 0.6 | 1.6 |
| #10 | NO | 10.6 | 6.2 | 3.8 | 14.1 | 1.7 | 8.1 | 4.2 | 3.4 | 11.2 | 1.8 |

A researcher wishes to know whether depressed patients who successfully cease alcohol consumption have a better prognosis than those who don't. In order to find out, he/she searches the entire profile database of patients on follow for depression to select patients for inclusion into one of two groups-test and control group. The test group consists of individuals who have completed the alcohol cessation program, while the control group consists of those who have not opted to cease alcohol consumption. The researcher now matches patients in the groups such that there is a patient with similar R, L and W factors in the test group for every patient with similar factors in the control group. Matching for factors is done for those contexts that are known to have a bearing on the long term prognosis of the depression, including the age-group, sex of the patient, the dosage of the drugs administered to the patient and most important, the initial risk state of the patient's depression. Of course, matching is not done for the context of alcohol cessation (Context 'CEASE ALCOHOL' in the chart), since this is what the researcher is interested in studying.

Matching is preferably done by the use of automated algorithms that match patients who exhibit similar values for the risk factors that are to be matched. The matching algorithm also excludes the patients whose data has—

1. low reliability, since a study done on unreliable data is bound to decrease the quality of the study
2. high resistance, since such patients are unlikely to adopt or continue the new management in any case. Management in these patients is directed towards decreasing the resistance first, and then attempt behavior modification.

3. very low risk factors of interest—the change in the values of R in the context of interest is likely to be so low, that the likelihood of errors is greatly increased in this case.

Chart 6 shows an algorithm for the automated assignment of patients to the two groups. Individuals whose risk factors and values meet allocation criteria as decided by the researcher are automatically assigned into the groups as shown below.

CHART 6

TEST GROUP

IF CEASE ALCOHOL = 'YES'
AND $R_1 > 2.5$
AND $R_2 > 2.0$
AND $R_3 > 1.5$
AND $L_{ALL} > 4.0$
AND $W_{ALL} < 3.0$
THEN PATIENT = 'TO TEST GROUP'
CONTROL GROUP

ELSE IF CEASE ALCOHOL = 'NO'
AND $R_1 > 2.5$
AND $R_2 > 2.0$
AND $R_3 > 1.5$
AND $L_{ALL} > 4.0$
AND $W_{ALL} < 3.0$
THEN PATIENT = 'TO CONTROL GROUP'
EXCLUDED GROUP-REASON LOW L VALUES

ELSE IF $L_{ALL} \leqq 4.0$
THEN PATIENT = 'EXCLUDED GROUP REASON: LOW L VALUES'
EXCLUDED GROUP-REASON HIGH W VALUES ELSE IF $W_{ALL} \geqq 3.0$
THEN PATIENT = 'EXCLUDED GROUP REASON: HIGH W VALUES'
EXCLUDED GROUP-REASON LOW R VALUES ELSE IF $R_1 < 2.5$
OR $R_2 < 2.0$
OR $R_3 < 1.5$
THEN PATIENT = 'EXCLUDED GROUP REASON: LOW R VALUES'

It is obvious that there may be more than one reason to exclude a patient from the study. On the basis of the exclusion criteria, patients are assigned to the groups as shown in Chart 7 below.

CHART 7

| INCLUDED PATIENTS | | |
|---|---|---|
| TEST GROUP | CONTROL GROUP | EXCLUDED PATIENTS REASON |
| #1 | #7 | LOW L VALUES #9 |
| #8 | #2 | HIGH W VALUES #6 |
| #3 | #5 | LOW R VALUES #4, #8 |

Once this is done, the researcher has two groups of patients who are comparable in all respects, except that one group has ceased alcohol consumption at that point of time, while the other group continues to consume alcohol. Now, the researcher analyzes the difference between the present R factors of the two groups. In addition, it is also necessary to verify that none of the patients enrolled in the study have developed an unacceptably high resistance or low reliability during the course of the study.

Standard statistical methods are used to test the level of significance of the R factors as a result of the alcohol cessation. R factors of more than one context, which are scored on the basis of replies, may be used to measure the improvement in the risk status of the patient. Alternatively, the R values are derived from standard questionnaires that score the risk status of the patient objectively e.g. SF12, SF36, Minnesota Living with Heart Failure Questionnaire, Geriatric Depression Scale. Alternatively, laboratory tests may be used to evaluate the effectiveness of the management e.g. in the case of blood glucose control, Serum $HB_{A1C}$ values, that give an indication on the long term (80-100 days) level of blood sugar control may be used. If there is a statistically significant benefit (which may not be attributed to chance alone) from these analyses, it is concluded that alcohol cessation in depressed patients is helpful in the treatment of their depression. In this manner a researcher is able to prove or refute earlier hypotheses.

The advantage in using the system for the purpose of research is that the method of storage of data in the form of R, L and W values is ideally suited to risk assessment. In case of doubt, since all inputted replies to queries would additionally be archived by the system, it is possible to validate the assigned R, L and W values. Further, since the data for patients over multiple healthcare facilities is stored in the same database format, it is possible to integrate the results over multiple healthcare facilities. This makes it convenient to conduct large multi-centre studies, and further validates the results of the study.

In addition, the cost of conducting the study is greatly reduced, since the data is already preformatted for the purpose of comparison. It is of importance to note that any context can be studied in relation to any other context over a large group of patients. It is also possible to conduct studies comparing the effectiveness of different healthcare facilities management protocols by a similar method. Further, it is possible to randomly assign patients to one of two groups (prospective randomized controlled trials), each receiving different treatments and comparing the effects of the different treatments. This information may be further added into the new protocols for better automated content assignment. So this method may also be used in the evaluation of different protocols of management in the system, and be used to refine the protocols assignment process in any group of patients.

Process Governing Dynamics

In view of the above, it is apparent that the provider utilizes a combination of automatically selected and manually assigned content to elicit further information from the monitored individuals. Automated content utilizes a combination of the level of risk of the patient, the immediacy/urgency of delivering the content to the individual, the individual's reliability and resistance, and the individual's profile variables such as comprehension capacity, motivational drivers, etc. Automatically assigned content is queued in the tasklist database, for communication with the individual at the next connection. However, the provider may also assign content manually from the report generator interface, and has the additional option of modifying, appending and deleting content from the tasklist database.

The monitoring application regularly scans the individual's entire profile and seeks variables, and combinations of variables within the profile, for which there are defined protocols within the protocols database. Protocols are program statements that instruct the monitoring application to perform actions 140 when a given set of conditions are fulfilled. Actions 140 include alerting the healthcare provider to the presence of a combination of variables that may signify an impending 'pre-acute' state in the patient. The protocol shown below is for patients with mood disorders. A gradually worsening mood over many days is often the first sign of an incoming depression in these patients. Since these patients are at risk for committing suicide in their depressed state, it is important that their mood fluctuations be continuously monitored, and that these individuals are prevented from deliberately harming themselves.

Protocol

---

(1) IF PATIENT REPLY RECEIVED = 'FALSE'
AND $MOOD_{RECENT}$ = 'FEELING TERRIBLE'
THEN ACTION: ALERT PROVIDER, 'PATIENT NOT RESPONDING'
(2) ELSEIF $MOOD_{CURRENT}$ = 'FEELING TERRIBLE'
AND $MOOD_{CURRENT-1}$ = 'FEELING FINE'
AND/OR $MOOD_{CURRENT-2}$ = 'FEELING FINE'
THEN ACTION: FOLLOW WORSENING_MOOD DIALOG
(3) ELSEIF $MOOD_{CURRENT}$ = 'FEELING TERRIBLE'
AND $MOOD_{CURRENT-1}$ = 'FEELING TERRIBLE'
AND $MOOD_{CURRENT-2}$ = 'FEELING TERRIBLE'
THEN ACTION: FOLLOW PERSISTENT_DYSPHORIA DIALOG
(4) ELSEIF $MOOD_{CURRENT}$ = 'FEELING FINE'
ANT $MOOD_{CURRENT-1}$ = 'FEELING GREAT'
AND $MOOD_{RECENT}$ = 'FEELING GREAT'
THEN ACTION: FOLLOW MOOD_SURVEILLANCE PROTOCOL

---

In the first condition in the protocol, the monitoring application is activated when replies to queries are not received in time by the system. Given that the patient has recently stated that he/she has been feeling terrible, the lack of reply is likely to suggest a worsening mood level in the patient, since patients who are very depressed are unable to sum up enough energy to even perform the activities of daily existence. The action here is to alert the provider, so that he/she may initiate personal contact with the patient, since dialogs are unlikely to be of any benefit (the patient has ceased responding to the remote apparatus)

The second condition of the protocol, if returned true, implies that the patient's mood has been worsening. This may be because of external factors, such as problems with family, and at the workplace, or may be without any apparent reason. The reason for the worsening mood is explored using the WORSENING_MOOD dialog. If it is determined that the patient's mood is worsening without any apparent reason, then such a patient is kept on close follow up. Alternatively, the provider may schedule a priority appointment with the patient.

The third condition of the protocol, if returned true, implies that the patient has been steadily feeling terrible. This may be because of the patient's failure to take medication or due to a recent event, or even due to the failure of the medication to act in the particular patient. The reason for the patient's persistently low mood is elucidated by the PERSISTENT_DYSPHORIA dialog.

In the fourth condition, the patient's mood has been deteriorating, though it is still at the level of 'feeling fine'. This patient would require more intensive monitoring for worsening mood, and the monitoring application switches the patient to the MOOD-SURVEILLLANCE_PROTOCOL, whereby there is more frequent communication between the patient and the system, and the threshold for alerting the provider to a worsening mood is lowered.

While the preferred embodiment of the invention has been illustrated and described, as noted above, many changes can be made without departing from the spirit and scope of the invention. Accordingly, the scope of the invention is not limited by the disclosure of the preferred embodiment.

The invention claimed is:

1. A remote health management system, the system comprising:
a central computer, the central computer further comprising program instructions, wherein said program instructions comprise (i) a monitoring application configured to generate (a) a motivational driver of an individual, (b) a comprehension capacity of the individual, and (c) a media selection of the individual, (ii) a task scheduler configured to generate a queue for executing specific tasks in a specified order, (iii) a content assignor configured to select dialogs based on a health condition of the individual, (iv) a dialog generator configured to generate specific dialogs from a dialog library based on said dialogs selected by said content assignor, (v) a script generator configured to generate scripts based on said specific dialogs, and (vi) a report generator configured to generate reports used by a healthcare provider to monitor a health condition of the individual;
a database in communication with the central computer, the database comprising (i) a protocol section, (ii) a profile section, (iii) a task list section, and (iv) a dialogs library section; and
a communication network connected to the central computer, the communication network further connected to a plurality of remote terminals,
wherein each of said remote terminals are in communication with (i) a monitoring device operated by the individual, (ii) an external data source through the communication network, (iii) a healthcare provider computer through the communication network, and (iv) a medical claims database of a managed care organization through the communication network,
wherein (i) each of the remote terminals is configured to establish a respective communication link with the central computer to enter a communications mode, and (ii) the central computer is configured to send the program instructions to the remote terminal corresponding to the individual in response to establishing the respective communication link,
wherein said remote health management system is configured such that (i) a medical condition of each individual is diagnosed, (ii) a risk-stratification is established of the individual in a group of individuals, and (iii) a treatment recommendation is developed for each individual based upon (a) the diagnosis of the individual and (b) the risk stratification assigned to the individual, (iv) said treatment recommendation is provided to the health care provider through said healthcare provider computer.

2. The remote health monitoring system of claim 1, wherein said monitoring application generates said profile section of said database.

3. The remote health monitoring system of claim 1, wherein said monitoring application scans the profile section of said database for correlation of data within specified parameters.

4. The remote health monitoring system of claim 1, wherein said monitoring application further comprises a confirmation program configured to send a confirmation signal to one or more of said plurality of remote terminals.

5. The remote health monitoring system of claim 1, wherein said monitoring application creates new protocols and said new protocols are added to the protocol section of said database.

6. The remote health monitoring system of claim 1, wherein said dialogs library section comprises dialog contents customized for said individual.

7. The remote health monitoring system of claim 1, wherein said dialogs library section comprises queries, replies, data files, and actions, wherein said actions comprise the next function to be performed for each of the possible replies.

8. The remote health monitoring system of claim 7, wherein said queries, said replies, and said data files are provided in a plurality of different languages.

9. The remote health monitoring system of claim 7, wherein said risk-stratification of said individual determines which of said queries, said replies, said data files, and said actions are presented to said individual.

10. The remote health monitoring system of claim 7, wherein said protocol section of said database comprises program statements that instruct the monitoring application to perform said actions when a specified condition is met.

11. The remote health monitoring system of claim 1, wherein said risk-stratification of said individual is used to determine a risk level of said individual of developing health related complications pertaining to said medical condition of said individual.

12. The remote health monitoring system of claim 1, wherein said communication network comprises wireless communication.

\* \* \* \* \*